United States Patent [19]

Heitmann et al.

[11] 4,177,670
[45] Dec. 11, 1979

[54] METHOD AND APPARATUS FOR MULTIPLE TESTING OF WRAPPERS OF CIGARETTES FOR POROSITY

[75] Inventors: Uwe Heitmann, Schwarzenbek; Heinz-Christen Lorenzen, Hamburg; Günter Wahle, Reinbek; Rolf Dahlgrün, Schwarzenbek, all of Fed. Rep. of Germany

[73] Assignee: Hauni-Werke Körber & Co. KG., Hamburg, Fed. Rep. of Germany

[21] Appl. No.: 883,370

[22] Filed: Mar. 6, 1978

Related U.S. Application Data

[63] Continuation-in-part of Ser. No. 859,950, Dec. 12, 1977, abandoned, which is a continuation-in-part of Ser. No. 840,562, Oct. 11, 1977, abandoned.

[30] Foreign Application Priority Data

Nov. 26, 1976 [DE] Fed. Rep. of Germany ....... 2653735

[51] Int. Cl.² ............................................. G01N 15/08
[52] U.S. Cl. ........................................................ 73/38
[58] Field of Search ................ 73/40, 41, 45, 45.1, 73/45.2, 38

[56] References Cited

U.S. PATENT DOCUMENTS

| | | | |
|---|---|---|---|
| 3,395,570 | 8/1967 | Kochalski | 73/45.2 |
| 3,690,149 | 9/1972 | Fezzi | 73/45.2 |
| 3,935,728 | 2/1976 | Doerman | 73/41 |
| 3,991,605 | 11/1976 | Reuland | 73/45.2 |
| 4,020,675 | 5/1977 | Hirsh | 73/41 |
| 4,047,421 | 9/1977 | Spiers et al. | 73/45 |

Primary Examiner—S. Clement Swisher
Attorney, Agent, or Firm—Peter K. Kontler

[57] ABSTRACT

The permeability of portions of or entire wrappers of successive filter cigarettes is tested with a gaseous fluid independently of the permeability of perforated portions of wrappers around the filter mouthpieces. Signals denoting the permeability of major portions of or entire wrappers are compared with a reference signal denoting the maximum permissible permeability, and the cigarettes having wrappers of excessive permeability are segregated from satisfactory cigarettes. Signals denoting the permeability of perforated wrapper portions are made visible to attendants or cause the generation or audible signals, for example, to facilitate proper adjustment of perforating instrumentalities if the permeability of perforated wrapper portions is too low. Alternatively, signals which denote the permeability of perforated wrapper portions are compared with a reference signal denoting the minimum acceptable or excessive permeability, and the cigarettes wherein the permeability of perforated wrapper portions is too low or excessive are segregated from other cigarettes. The cigarettes are moved sideways in the course of measurement of the permeability of their wrappers, and the permeability of major portions of or entire wrappers can be ascertained simultaneously with, prior or subsequent to measurement of permeability of perforated wrapper portions. The perforations are provided for the purpose of admitting atmospheric air into the column of tobacco smoke.

45 Claims, 10 Drawing Figures

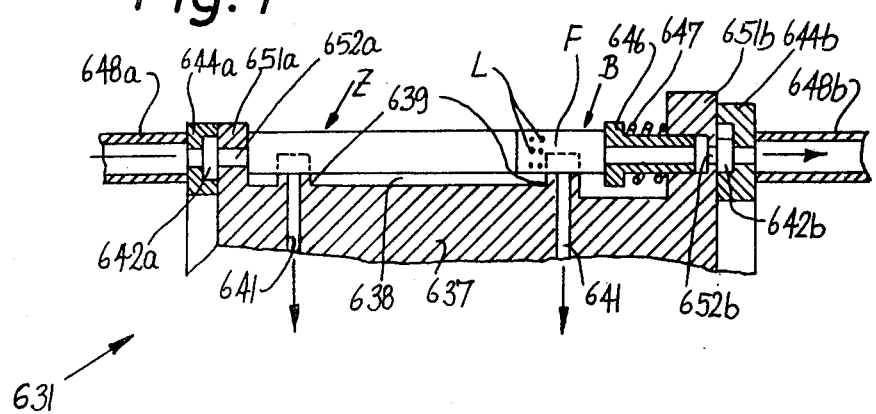
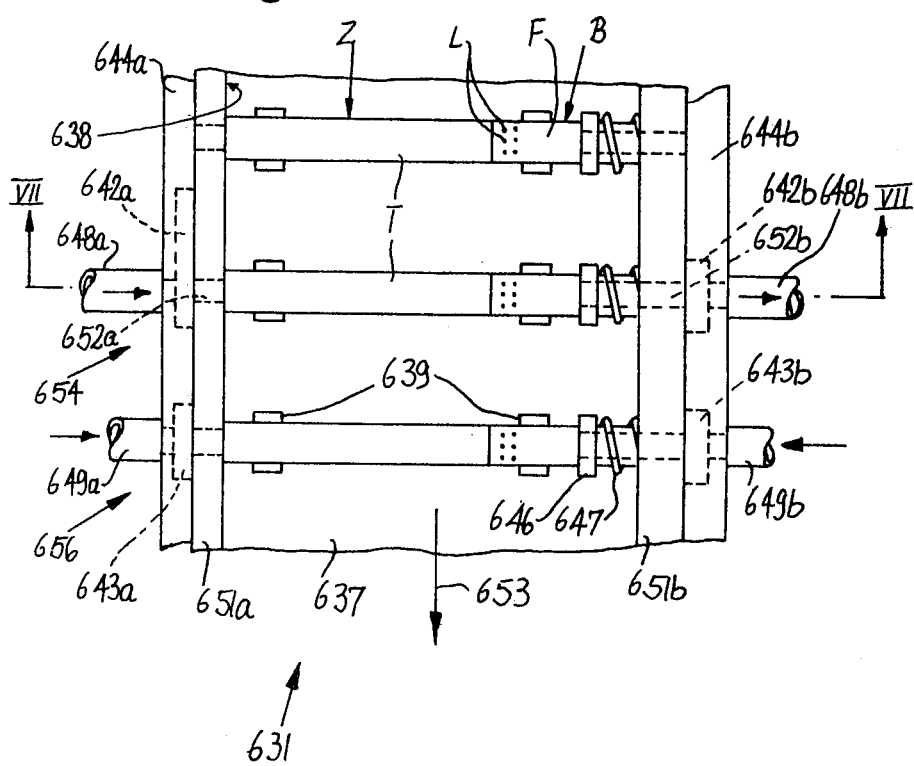

METHOD AND APPARATUS FOR MULTIPLE TESTING OF WRAPPERS OF CIGARETTES FOR POROSITY

CROSS-REFERENCE TO RELATED APPLICATION

This is a continuation-in-part of our copending application Ser. No. 859,950 filed Dec. 12, 1977, now abandoned. The application Ser. No. 859,950 is a continuation-in-part of our abandoned application Ser. No. 840,562 filed Oct. 11, 1977.

BACKGROUND OF THE INVENTION

The present invention relates to a method and apparatus for testing the wrappers of rod-shaped articles (including plain or filter-tipped cigarettes, cigars, cigarillos and cheroots as well as filter rod sections) which constitute or form part of smokers' products. More particularly, the invention relates to a method and apparatus for ascertaining the permeability of wrappers of rod-shaped articles (hereinafter referred to as cigarettes or filter cigarettes) of the type wherein each wrapper includes a portion of greater (predetermined) permeability so that it allows cool atmospheric air to enter the column of tobacco smoke flowing into the smoker's mouth.

It is already known to provide the wrappers of cigarettes with holes or perforations which admit cool atmospheric air into the column of tobacco smoke. The perforated portions of wrappers constitute the so-called climatic zones which are normally adjacent to unlighted ends of the cigarettes. For example, the wrapper of a filter cigarette will be provided with perforations in that portion which surrounds or is closely adjacent to the mouthpiece; this insures that cool atmospheric air will flow into the column of tobacco smoke regardless of the length of non-combusted portion of the tobacco-containing part of the smokers' product. Devices which can be used to perforate selected portions of wrappers of filter cigarettes or the like are disclosed, among others, in commonly owned copending applications Ser. Nos. 852,962 filed Nov. 18, 1977 by Heitman et al.; 841,108 filed Oct. 11, 1977 by Wahle et al.; and 864,441 filed Dec. 27, 1977 by Lüders et al.

Many manufacturers of smokers' products demand that the machines which produce cigarettes, cigars or cigarillos be equipped with perforating devices so as to allow a predetermined quantity of atmospheric air to mix with tobacco smoke which flows toward the mouth. The admixture of atmospheric air to smoke is considered to be desirable because it is believed to reduce health hazards which are assumed to result from smoking of tobacco by controlling the amount of nicotine and condensates in the smoke. The packages for cigarettes or other smokers' products must bear information indicating the nicotine content, the tar content and the percentage of certain other ingredients, and the manufacturer is responsible for the accuracy of such information. One of the factors which influence the quantity of nicotine and condensates in the column of tobacco smoke is the percentage of admitted atmospheric air; therefore, it is important to insure that the percentage of admitted air will invariably equal or even slightly exceed a predetermined minimum acceptable value. Consequently, it is necessary to ascertain whether or not the combined cross-sectional area of perforations in the wrappers suffices to guarantee admission of the minimum required quantity of atmospheric air. Furthermore, it is desirable to ascertain the permeability of a finished wrapper (i.e., of the tubular wrapper of a filter cigarette or the like) because this is the only reliable mode of determining the permeability of perforated wrapper portions. For example, certain perforations can be clogged by particles of tobacco or filter material so that, even if the permeability of wrapping material upstream of the wrapping station is clearly adequate, the permeability of perforated portion of the finished wrapper will be too low. Alternatively, the combined cross-sectional area of intentionally produced perforations may be satisfactory or even too low, but the permeability of the entire wrapper will be too high because the wrapper exhibits an open seam and/or one or more holes other than the intentionally produced perforations.

Automatic testing of wrappers of cigarettes or the like for the presence of open seams, holes, frayed ends and other defects is known for nearly two decades. The first successful automatic testing apparatus is disclosed in commonly owned U.S. Pat. No. 3,408,858 to Heinz Kaeding. As a rule, one establishes a pressure differential between the interior and exterior of the wrapper. The pressure differential decreases when the wrapper is defective, e.g., due to the presence of a partly open seam. This is detected by a transducer which furnishes signals to a signal comparing stage (e.g., a threshold circuit) which actuates an ejector when the intensity or another characteristic of the signal is indicative of a defective article. The ejector thereupon segregates each defective article from satisfactory articles, for example, by directing streams of compressed air against the ends or sides of defective articles. Presently known testing apparatus are sufficiently accurate to effect the segregation of cigarettes or analogous rod-shaped articles having wrappers which are defective because their permeability exceeds the acceptable permeability by a value corresponding to that which is attributable to the presence of a hole with a diameter of approximately one millimeter. Deviations which are less pronounced cannot be ascertained with a requisite degree of accuracy and reproducibility because the results of tests are often or invariably influenced by highly unpredictable factors such as unequal sealing of wrapper ends on successive articles during testing, deviation of density of the tobacco filler from an optimum value, wear upon moving parts of the testing apparatus, clogging of narrow passages in such apparatus by tobacco dust or other foreign matter and/or others. On the other hand, the increased permeability of intentionally perforated wrappers of filter cigarettes or the like is less pronounced than that permeability which is attributable to the presence of a hole with a diameter of one millimeter. Moreover, it is desirable to insure that the permeability of intentionally perforated portions of the wrappers should not deviate from (above or below) an optimum permeability by more than two percent.

OBJECTS AND SUMMARY OF THE INVENTION

An object of the invention is to provide a novel and improved method of ascertaining the permeability of wrappers of rod-shaped articles which constitute or form part of smokers' products and wherein predetermined portions of wrappers must exhibit a predetermined permeability.

Another object of the invention is to provide a method which insures the detection of all articles whose wrappers exhibit excessive permeability (for example, due to the presence of large holes or open seams) as well as the detection of articles wherein the permeability of intentionally perforated predetermined wrapper portions deviates (upwardly or downwardly) from an optimum value.

A further object of the invention is to provide a novel and improved method of multiple testing of wrappers of cigarettes or the like.

An additional object of the invention is to provide a method which allows for multiple testing of cigarettes or analogous rod-shaped articles at the rate at which such articles are produced in or issue from a modern high-speed maker, e.g., a filter cigarette making machine which turns out up to and in excess of 70 filter cigarettes per second.

Still another object of the invention is to provide a novel and improved apparatus for the practice of the above outlined method.

A further object of the invention is to provide a compact and relatively simple apparatus which can be readily installed in or combined with existing makers of cigarettes or the like.

One feature of the invention resides in the provision of a method of testing the wrappers of rod-shaped articles which constitute or form part of smokers' products. The method comprises the steps of measuring the permeability of at least the major portion of the wrapper of each of a series of successive rod-shaped articles, comparing the measured permeability with a predetermined value denoting the maximum permissible permeability of such portions of the wrappers, measuring the permeability of predetermined portions of the wrappers of the series of articles, and generating signals denoting the permeability of the predetermined wrapper portions. The predetermined wrapper portions are preferably those which are provided with holes or perforations prior to the last mentioned measuring step, and such portions are preferably adjacent to those ends of plain or filter cigarettes, cigars or cigarillos which are inserted into the mouth during smoking whereby the holes allow a predetermined quantity of atmospheric air to flow into the column of tobacco smoke as soon as a cigarette or the like is lighted and during the entire interval of burning while the length of the article decreases to that of a stub.

The method preferably further comprises the step of moving the articles of the series sideways along a predetermined path in the course of the measuring steps, and each measuring step preferably comprises establishing a pressure differential between the interior and exterior of the respective wrappers. The pressure differrential which is established in the course of the first mentioned measuring step may but need not deviate from the pressure differential which is established in the course of the last mentioned measuring step. The pressure at the exterior of the wrappers can exceed the pressure in the interior of the wrappers, or vice versa.

The signal generating step may include generating signals denoting the average permeability of a plurality of successively tested predetermined wrapper portions (preferably of a number of predetermined wrapper portions which travel along a selected portion of the path per unit of time). Alternatively, the signal generating step may include generating a discrete signal for the predetermined wrapper portion of each article of the series. In the latter instance (or at least in the latter instance), the method preferably further comprises the step of comparing the discrete signals with a reference signal which denotes the minimum acceptable permeability and/or a reference signal denoting the maximum permissible permeability of the predetermined wrapper portions.

The first and last mentioned measuring steps can be carried out in discrete first and second portions of the path (whereby the first mentioned measuring step precedes the last mentioned measuring step, or vice versa), or in one and the same portion of the path. The major portion of each wrapper (i.e., that portion which is monitored in the course of the first measuring step) may include the predetermined portion of the respective wrapper; alternatively, the permeability of the predetermined portion of each wrapper is measured solely in the course of the last mentioned measuring step. As a rule, the predetermined wrapper portion will constitute a relatively small or minute part of the respective wrapper. For example, such predetermined portion may constitute that part of the wrapper which surrounds the filter mouthpiece of a filter cigarette, cigar or cigarillo or a relatively small part of the wrapper of the filter mouthpiece.

The method may further comprise the step of segregating from the series those articles whose wrappers exhibit a permeability exceeding the maximum permissible permeability. Also, the method may comprise the additional steps of comparing the signals with a reference signal which denotes the minimum acceptable permeability of predetermined wrapper portions and/or with a reference signal which denotes the maximum permissible permeability of predetermined wrapper portions, and segregating from the series those articles wherein the permeability of predetermined wrapper portions is less than the minimum acceptable permeability or exceeds the maximum permissible permeability.

A slightly modified method, which can be resorted to for even more accurate determination of predetermined wrapper portions whose permeability is excessive or insufficient, includes the additional step of converting (e.g., in a suitable electronic averaging circuit) a plurality (preferably a constant number) of successive signals denoting the permeability of predetermined portions of wrappers whose permeability is less than the predetermined permeability into a second signal which denotes the average permeability of the respective (preferably constant) number of predetermined wrapper portions. The converting step may include modifying the second signals upon completion of each second measuring step so that the second signal continuously denotes the average permeability of the constant number of predetermined wrapper portions including the last-tested predetermined wrapper portions. This can be achieved by connecting the input of the averaging circuit with a suitable signal storing circuit having a plurality of stages whereby the stage which stores the signal for the longest interval of time erases the stored signal when the signal storing circuit receives a signal denoting the permeability of the last-tested predetermined wrapper portion.

The just discussed modified method preferably further comprises the step of comparing the second signal with a reference signal denoting the minimum acceptable or the maximum permissible average permeability of the constant number of predetermined wrapper portions to thus detect those predetermined wrapper portions whose permeability is too low or excessive. The modified method may further comprise the step of segregating from other articles at least some articles which include predetermined wrapper portions forming part of a constant number of predetermined wrapper portions whose average permeability is less than the minimum acceptable average permeability or exceeds the maximum permissible average permeability. If desired, the modified method can include the step of segregating at least some articles whose predetermined wrapper portions form part of a constant number whose average permeability is outside of a predetermined range of acceptable permeabilities, i.e., whose average permeability is excessive or too low.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 7 is a fragmentary axial sectional view of a modified conveyor, the section being taken in the direction of arrows as seen from the line VII—VII of FIG. 8;

FIG. 8 is a fragmentary plan view of the modified conveyor;

DESCRIPTION OF THE PREFERRED EMBODIMENTS

Figure 1:
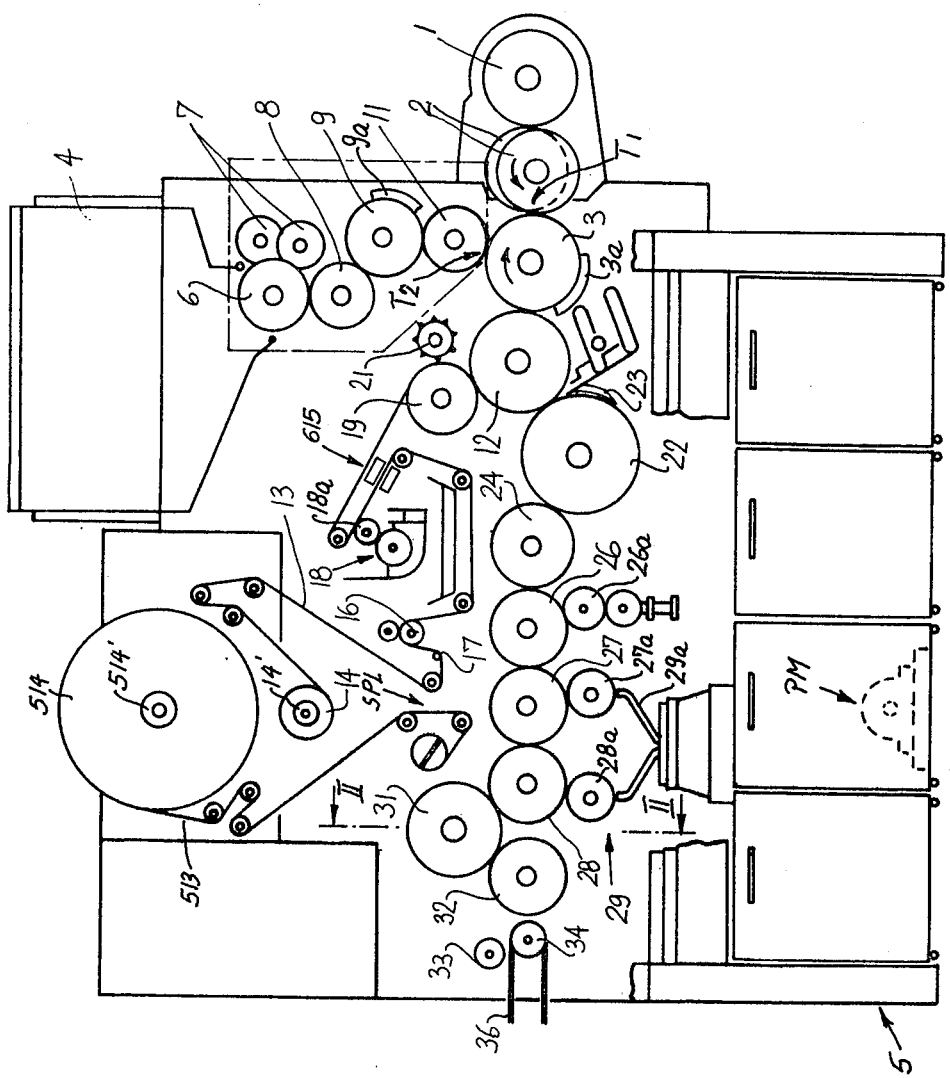
FIG. 1 is a schematic elevational view of a filter cigarette making machine including a testing apparatus which embodies one form of the invention.

FIG. 1 shows a filter cigarette making machine of the type known as MAX S (produced by the assignee of the present application). The machine is directly coupled to a maker of plain cigarettes of unit length, e.g., to a machine known as GARANT (trademark) also produced by the assignee of the present application. The maker comprises a rotary drum-shaped row forming conveyor 1 which is mounted in or on the frame 5 of the filter cigarette making machine and has peripheral flutes for continuous delivery of two rows of plain cigarettes of unit length. The flutes of the conveyor 1 are parallel to its axis, i.e., the cigarettes are transported sideways. The cigarettes of one row are admitted into the oddly numbered flutes and the cigarettes of the other row are admitted into the evenly numbered flutes of the conveyor. Furthermore, the cigarettes of one row are adjacent to one axial end and the cigarettes of the other row are adjacent to the other axial end of the conveyor 1.

The filter cigarette making machine comprises a pair of rotary drum-shaped aligning conveyors 2 which are mounted in the frame 5 adjacent to the row forming conveyor 1 and have peripheral flutes for sidewise transport of plain cigarettes toward a transfer station T1. One of the conveyors 2 receives successive plain cigarettes of one row and the other conveyor 2 receives successive plain cigarettes of the other row. The conveyors 2 are driven at different speeds and/or transport the plain cigarettes of the respective rows through different distances so that each flute of a rotary drum-shaped assembly conveyor 3 which arrives at the transfer station T1 receives a pair of coaxial plain cigarettes of unit length. The plain cigarettes of each pair are separated from each other by a gap having a width which at least equals the length of a filter rod section or mouthpiece of double unit length.

The upper portion of the frame 5 supports a magazine 4 for filter rod sections of six times unit length. The outlet of the magazine 4 receives a portion of a rotary drum-shaped severing conveyor 6 having peripheral flutes which remove filter rod sections from the magazine 4 and transport them past two rotary disk-shaped knives 7 which are staggered with respect to each other, as considered in the axial and circumferential directions of the conveyor 6. The latter cooperates with the knives 7 to subdivide each filter rod section of six times unit length into sets of three coaxial filter rod sections of double unit length. The filter rod sections of each set are transferred into the peripheral flutes of three rotary drum-shaped staggering conveyors 8 (only one shown) which rotate at different speeds and/or transport the respective filter rod sections of double unit length through different distances to thereby stagger the sections in the circumferential direction of the illustrated conveyor 8. The staggering conveyors 8 deliver discrete filter rod sections of double unit length into successive flutes of a rotary drum-shaped shuffling conveyor 9 which cooperates with two stationary cams 9a to convert the filter rod sections into a single row wherein each preceding section is in exact register with the next-following section. Successive sections of the thus obtained row are delivered into successive flutes of a rotary drum-shaped accelerating conveyor 11 which deposits the sections in successive flutes of the assembly conveyor 3 at a second transfer station T2 preceding the station T1. Each inserted filter rod section of double unit length is positioned in such a way that it is flanked by two coaxial plain cigarettes of unit length after the respective flute of the conveyor 3 advances beyond the station T1. The thus obtained groups of three coaxial rod-shaped articles each (a filter rod section of double unit length and two plain cigarettes of unit length) are thereupon caused to move through the gap between two stationary condensing cams 3a which engage the outer ends and cause the inner ends of plain cigarettes to move into actual abutment with the respective ends of the associated filter rod section. The condensed groups are delivered into the flutes of a rotary drum-shaped transfer conveyor 12.

The frame 5 of the filter cigarette making machine further supports a spindle 14' for a roll 14 of convoluted wrapping material which constitutes an elongated web 13 consisting of cigarette paper, artificial cork or the like. The web 13 is drawn off the roll 14 by two advancing rolls 16 at least one of which is driven by the prime mover PM of the filter cigarette making machine and the other of which is preferably biased against the one roll. Successive increments of the web 13 are caused to pass along the relatively sharp edge of a curling device 17 of the type disclosed in the commonly owned U.S. Pat. No. 3,962,957 granted June 15, 1976 to Alfred Hinzmann. The purpose of the curling device 17 is to eliminate and/or equalize internal stresses in the material of the web 13. One side of the running web 3 is coated with a suitable adhesive by the rotary applicator 18a of a paster 18 which is installed in the frame 5 downstream of the advancing rolls 16. The leader of the web 13 adheres to the periphery of a rotary suction drum 19 which cooperates with a rotary knife 21 to subdivide the web 13 into a succession of discrete adhesive-coated uniting bands. Such bands are attached to successive groups of rod-shaped articles on the transfer conveyor 12, preferably in such a way that each uniting band extends tangentially of the respective group and adheres to the respective filter rod section as well as to the inner end portions of the adjacent plain cigarettes.

A second spindle 514' supports a roll 514 consisting of convoluted wrapping material which constitutes an elongated web 513. The leader of the web 513 is located at a splicing station SPL which includes means for attaching the leader of the web 513 to the running web 13 when the diameter of the roll 14 is reduced to a predetermined minimum value. The splicing device at the station SPL may be of the type disclosed in commonly owned U.S. Pat. No. 3,586,006 granted June 22, 1971 of Gerd-Joachim Wendt.

Successive groups in the flutes of the transfer conveyor 12 (each such group carries a discrete uniting band) are delivered to a rotary drum-shaped wrapping conveyor 22 which cooperates with a stationary or mobile rolling device 23 to roll successive groups around their respective axes and to thus convert the respective uniting bands into tubes which sealingly surround the filter rod sections and the inner ends of plain cigarettes of the respective groups, i.e., each such group is converted into a filter cigarette of double unit length. The wrapping conveyor 22 delivers successive filter cigarettes of double unit length into the flutes of a rotary drum-shaped heating or drying conveyor 24 which insures that the adhesive on each tube sets prior to transfer into the flutes of a rotary drum-shaped severing conveyor 26 cooperating with a rotary disk-shaped knife 26a which severs each filter cigarette of double unit length midway across the tube so that such cigarettes yield pairs of coaxial filter cigarettes Z (FIG. 2) of unit length (hereinafter called cigarettes for short). Defective cigarettes (e.g., those without a filter plug or tobacco-containing portion) are ejected during travel along the periphery of the severing conveyor 26.

The conveyor 26 delivers pairs of cigarettes to the rotary drum-shaped conveyor 27 of a turn-around device 29 of the type disclosed in commonly owned U.S. Pat. No. 3,583,546 granted June 8, 1971 to Gerhard Koop. One cigarette of each pair is transferred onto a second conveyor 27a and is inverted through 180 degrees by one of several orbiting arms 29a. The other cigarettes of successive pairs are transferred into alternate flutes of a third rotary drum-shaped conveyor 28 of the device 29. A fourth conveyor 28a of the device 29 delivers inverted cigarettes into empty flutes of the conveyor 28 so that the inverted cigarettes are disposed between neighboring non-inverted cigarettes and the cigarettes form a single row wherein the filter mouthpieces of all cigarettes face in the same direction.

The conveyor 28 delivers successive cigarettes of the single row to a rotary drum-shaped conveyor 31 forming part of a testing apparatus wherein the cigarettes are monitored to ascertain whether or not their wrappers are satisfactory. Cigarettes having defective wrappers are segregated from satisfactory cigarettes during travel with a rotary drum-shaped conveyor 32 which is located downstream of the conveyor 31 and delivers satisfactory cigarettes onto the upper reach of a belt conveyor 36 trained over pulleys 34 (one shown). The illustrated pulley 34 cooperates with a rotary braking drum 33. The conveyor 36 delivers satisfactory cigarettes into storage, into chargers, to a pneumatic sender or directly into the magazine of a packing machine, not shown.

Figure 2:
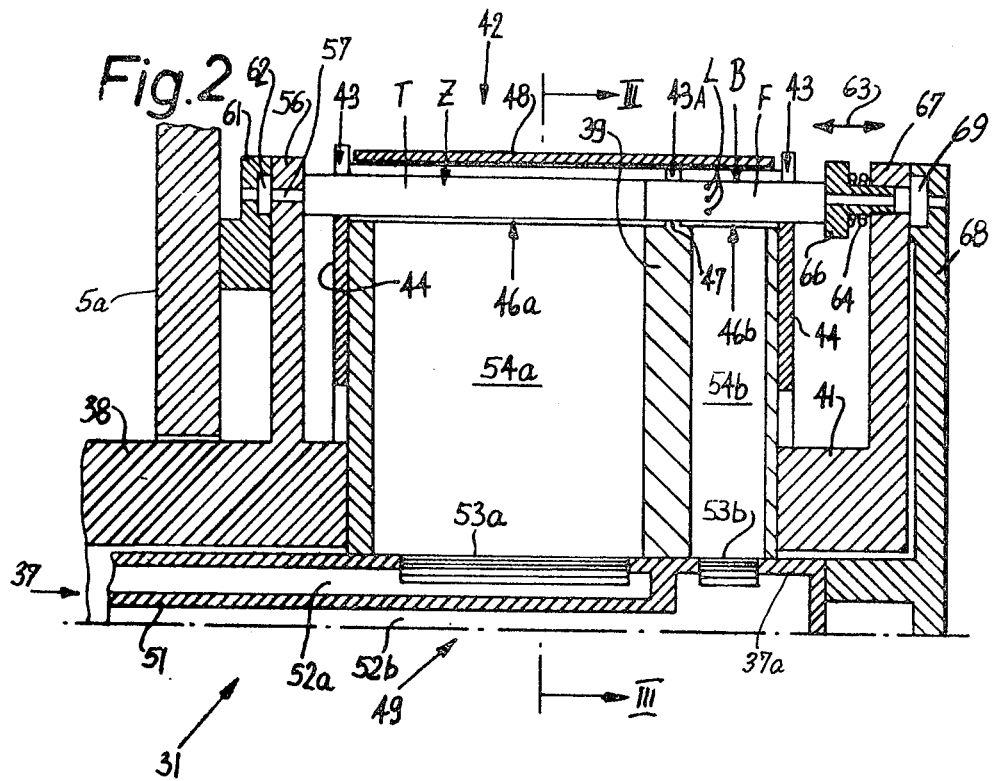
FIG. 2 is an enlarged fragmentary axial sectional view of a conveyor which forms part of the testing apparatus, the section being taken in the direction of arrows as seen from the line II—II of FIG. 1.
Figure 3:
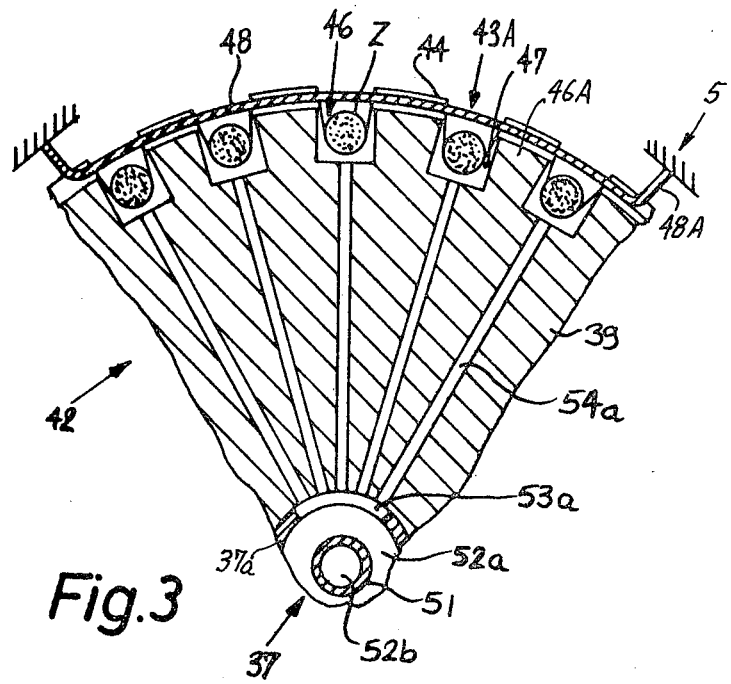
FIG. 3 is a fragmentary transverse vertical sectional view as seen in the direction of arrows from the line III—III of FIG. 2.

FIGS. 2 and 3 illustrate certain details of the testing apparatus which includes the conveyor 31 of FIG. 1. In many respects, the testing apparatus which is used in the filter cigarette making machine of FIG. 1 operates (or can operate) in a manner known from presently used testing apparatus for rod-shaped articles which constitute or form part of smokers' products. The operation is based on the principle that one establishes a pressure differential between the interior and exterior of the wrapper and monitors the magnitude or extent of such pressure differential. The pressure can be higher in the interior of or around the wrapper, and the monitoring step can include measuring the rise of pressure at the lower-pressure side and/or measuring the drop of pressure at the higher-pressure side of wrapper. As a rule, the testing fluid is air; however, it is clear that many other gases can be used with equal advantage. A suitable testing apparatus which can be used, with certain modifications, for the purposes of the present invention is disclosed in commonly owned U.S. Pat. No. 3,948,084 granted Apr. 6, 1976 to Bob Heitmann et al. to which reference may be had for all such details which are not fully shown in the drawing of the present application.

FIGS. 2 and 3 show a hollow shaft 37 which supports the components of the testing conveyor 31. Such components include three coaxial rotary members 38, 39 and 41 which together constitute a drum-shaped main body portion 42 of the conveyor. The means for transmitting torque from the prime mover PM (FIG. 1) to the main body portion 42 is of conventional design. The median rotary member 39 is flanked by two disks 44 whose peripheral portions define annuli of article-receiving cradles or sockets 43. Each socket 43 of the left-hand disk 44 of FIG. 2 is in register with a socket 43 of the right-hand disk 44. The conveyed articles are filter cigarettes Z of unit length; each such cigarette comprises a filter mouthpiece F of unit length and a plain cigarette T of unit length. These parts are sealingly secured to each other by one-half B of a convoluted uniting band which is obtained in response to severing of the web 13 in a manner as shown in FIG. 1. The rotary member 39 is formed with peripheral cutouts or recesses 46 each of which is disposed between and aligned with two registering sockets 43. Still further, the rotary member 39 has an external ring 47 with an annulus of cradles 43A which receive the filter mouthpieces F in regions close to the adjacent inner ends of the plain cigarettes T. The cradles 43A can be said to constitute partitions which divide the respective recesses 46 into first and second compartments 46a and 46b. The compartments 46a receive the major portions of plain cigarettes T and the compartments 46b receive portions of filter mouthpieces F of cigarettes Z in the respective recesses 46. The convoluted uniting bands or tubes B which surround the filter mouthpieces F and the adjacent inner end portions of plain cigarettes T have portions of desired permeability which is attributable to the provision of holes L adjacent to the right-hand side of the cradle 43A shown in FIG. 2. The manner in which the holes can be formed in the uniting bands B, either prior or subsequent to draping of uniting bands around the respective groups of coaxial articles is disclosed, for example, in commonly owned copending application Serial No. 841,108 of Wahle et al. and in commonly owned copending application Ser. No. 864,441 of Lüders et al. Reference may be had to these commonly owned applications for the details of perforating devices which can be employed to provide the bands B with predetermined portions of desired permeability. The application of Wahle et al. discloses that the perforating device may comprise needles, punching tools, spark generators and/or one or more lasers. Such device can be located between the roll 14 and drum 19 of FIG. 1 or adjacent to one of the conveyors which transport groups or rod-shaped articles, filter cigarettes of double unit length or filter cigarettes Z of unit length toward the conveyor 31. For example, a perforating device employing one or more sets of needles can be placed adjacent to the path of freshly formed filter cigarettes of double unit length on the wrapping conveyor 22 of FIG. 1.

The testing apparatus which includes the structure of FIGS. 2 and 3 further comprises an arcuate sealing element or shroud 48 which is disposed between the disks 44 and overlies the open outer ends of several neighboring recesses 46. The shroud 48 is secured (preferably pivoted) to the frame 5, as at 48A. The concave inner side of the shroud 48 is preferably closely adjacent to the projections 46A between neighboring recesses 46 of the rotary member 39 so that the compartments 46a, 46b which travel along the concave side of the shroud 48 are substantially sealed from the surrounding atmosphere. FIG. 3 shows that the width of gaps between the shroud 48 and the rotary member 39 is negligible.

The pressure of fluid in compartments 46a which travel along the concave inner side of the shroud 48 is different from the pressure of fluid in the associated compartments 46b. The means 49 for maintaining the pressure in compartments 46a, 46b at different levels includes an annular partition or wall 51 which is provided in and divides the interior of the shaft 37 into two discrete spaces 52a and 52b. The spaces 52a, 52b are connected with the suction intake of a blower or another suitable source 76 of compressed gas (see FIG. 4). The cylindrical outer wall 37a of the shaft 37 (which is stationary) has a relatively long slot 53a which is parallel to the axis of the shaft 37 and establishes communication between the space 52a and a certain number (including one) of channels 54a machined into the rotary member 39. Each channel 54a communicates with a discrete compartment 46a. The outer wall 37a of the shaft 37 is further formed with a second slot 53b which may but need not be aligned with the slot 53a and connects the space 52b with a certain number (including one) of channels 54b also machined into the rotary member 39 and each communicating with a different compartment 46b. The illustrated arrangement is such that, when a compartment 46a communicates with the space 52a, the aligned compartment 46b does not communicate with the space 52b.

The rotary member 38 has a ring-shaped flange 56 with bores or holes 57 each of which is in register with a socket 43 in the adjacent disk 44. The flange 56 rotates with respect to a stationary valve plate 61 having an arcuate groove 62 which communicates with successive holes 57 when the conveyor 31 rotates about the axis of the shaft 37. The groove 62 receives compressed testing fluid or atmospheric air. If the groove 62 receives compressed testing fluid, it is connected with a suitable source, e.g., the pressure outlet of the aforementioned blower 76, so that such fluid penetrates into the interior of the wrapper of the cigarette Z which advances past the groove 62. The flange 56 seals the left-hand ends of the wrappers of cigarettes Z save for the relatively small regions which register with the respective holes 57. The valve plate 61 is biased against the outer side of the flange 56 to prevent uncontrolled escape of testing fluid from or uncontrolled admission of atmospheric air into the groove 62. A member 5a of the frame 5 supports the valve plate 61 adjacent to the path of movement of the flanbge 56.

The rotary member 41 has a flange 67 which carries an annulus of reciprocable sealing elements 66 here shown as nipples which are biased by helical springs 64 so that they bear against the right-hand ends of wrappers of cigarettes Z on the conveyor 31. Each nipple 66 is in register with a socket 43 in the adjacent disk 44, and each such nipple is movable in directions indicated by the double-headed arrow 63. A suitable stationary cam (not specifically shown) is mounted in the frame 5 and cooperates with roller followers of the nipples 66 to retract the nipples ahead of the transfer station between the conveyors 28, 31 and again ahead of the transfer station between the conveyors 31, 32 so as to allow for unobstructed introduction of cigarettes Z into the respective sockets 43 and cradles 43A. Once a cigarette Z enters the respective sockets and the respective cradles, the cam allows the springs 64 to expand and to move the nipples 66 into sealing engagement with the adjacent ends of the wrappers of cigarettes Z; at the same time, the nipples 66 push the respective cigarettes Z against the flange 56. Alternatively, the nipples can be moved by a wobble plate in a manner as disclosed in the aforementioned U.S. Pat. No. 3,948,084 to Heitmann et al.

Each nipple 66 has an axial passage which can admit compressed testing fluid or atmospheric air into the respective end of the aligned wrapper. Such compressed fluid or uncompressed atmoshperic air is admitted by an arcuate groove 69 in a second stationary valve plate 68 which is outwardly adjacent to the flange 67. Each of the grooves 62, 69 can be connected with a device which measures the pressure of testing fluid and furnishes appropriate signals indicative of the measured pressure.

Figure 4:
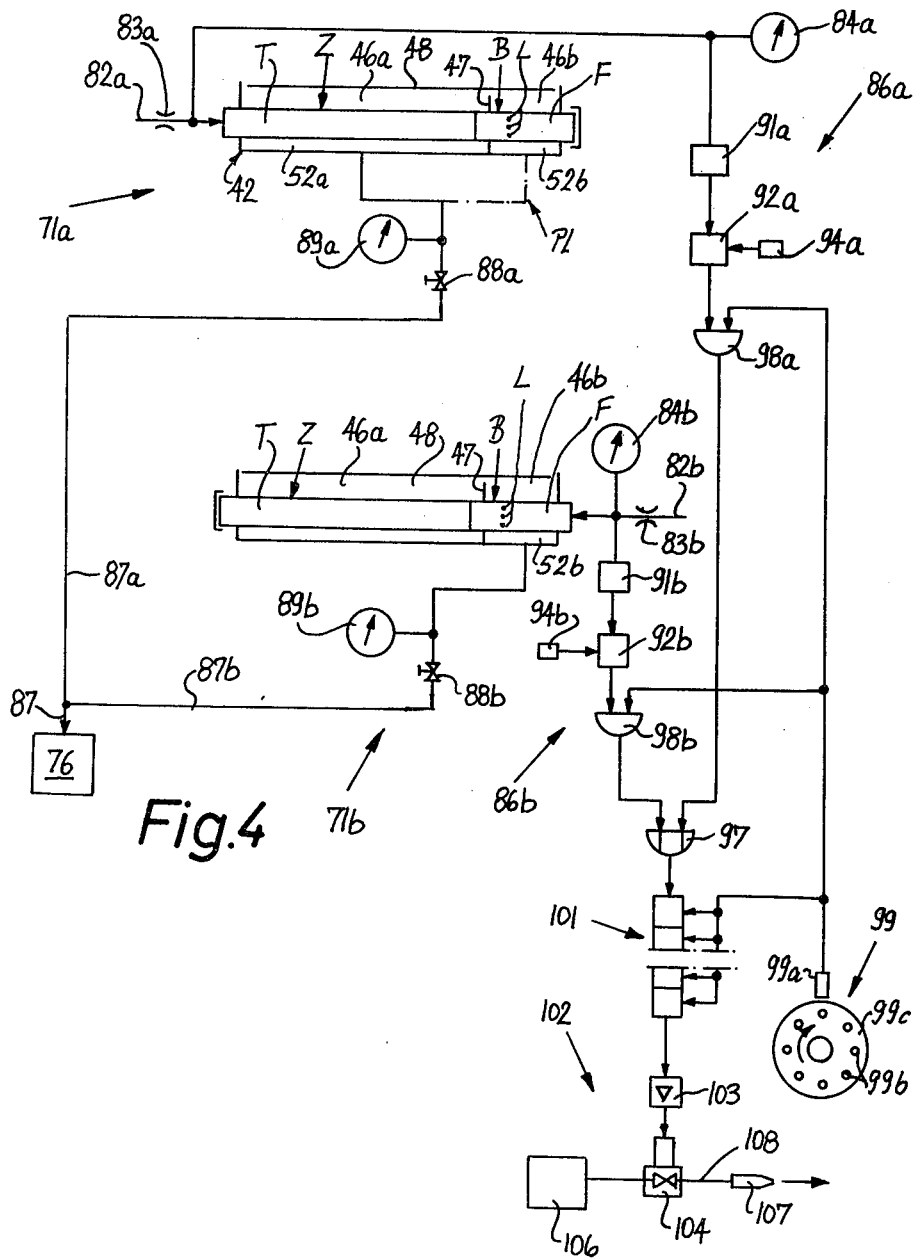
FIG. 4 is a diagrammatic view of the testing apparatus which includes the conveyor of FIGS. 2 and 3.

FIG. 4 shows that the testing apparatus which includes the structure of FIGS. 2 and 3 is composed of two testing devices or units 71a and 71b and that the conveyor 31 is common to both testing devices. The provision of two testing devices is due to the fact that the length of the grooves 62, 69 in the valve plates 61, 68 is less than the distance between the axes of two neighboring cigarettes Z (as considered in the circumferential direction of the conveyor 31) and that the two grooves are angularly offset with respect to each other by a distance equal to one or several distances between the axes of two neighboring cigarettes. In other words, the nipples 66 travel past an ungrooved portion of the stationary valve plate 68 (so that the outer ends of their axial bores are sealed) while the registering holes 57 of the flange 56 communicate with the groove 62, and the outer ends of the holes 57 are sealed by the valve plate 61 while the bores of the registering nipples 66 communicate with the groove 69 of the valve plate 68.

The angular distance between the slots 53a and 53b equals that between the grooves 62 and 69. Therefore, the suction intake of the blower 76 communicates with a given channel 54a and the respective compartment 46a before the compartment 46b of the same recess 46 communicates with the space 52b via slot 53b. The suction intake of the blower 76 is connected with a suction pipe 87 having a first branch 87a which is connected to the space 52a and a second branch 87b which is connected to the space 52b. The branches 87a, 87b respectively contain pressure regulating valves 88a, 88b (these valve form part of the aforementioned means 49 for maintaining the pressure in compartment 46a, 46b at different levels) and pressure gauges 89a, 89b. The adjustment of the valves 88a, 88b is such that the pressure in the space 52a is considerably higher than in the space 52b, i.e., the evacuation of air from a compartment 46b (when such compartment communicates with the space 52b) is much more pronounced than the evacuation of air from that compartment 46a which communicates with the space 52a. Thus, the testing device 71b is more sensitive than the testing device 71a.

The groove 62 of the valve plate 61 is connected to the atmosphere by way of a pipe 82a which contains a preferably adjustable flow restrictor 83a, a pressure gauge 84a whose inertia is high (the gauge 84a may be of the type known as encapsulated spring manometer), and the element 91a of a pressure measuring or evaluating circuit 86a.

The groove 69 of the valve plate 68 communicates with the atmosphere by way of pipe 82b. The pipe 82b contains a preferably adjustable flow restrictor 83b, a high-inertia pressure gauge 84b and the element 91b of a second pressure measuring or evaluating circuit 86b. The construction of the measuring or evaluating circuit 86b is substantially identical with that of the circuit 86a save for the setting of a threshold circuit 92b. The element 91a of the circuit 86a is a transducer (e.g., an electropneumatic transducer of the type disclosed in commonly owned U.S. Pat. No. 3,412,856 granted to Esenwein). The output of the tranducer 91a is connected with one input of a threshold circuit 92a another input of which receives a reference signal from a suitable source 94a (e.g., an adjustable potentiometer). The output of the threshold circuit 92a is connected with one input of an AND-gate 98a another input of which is connected with the proximity switch 99a of a pulse generator 99 driven by the prime mover PM of FIG. 1 in synchronism with the conveyor 31 and having a rotary disk 99c with a plurality of magnets 99b which cause the switch 99a to transmit signals at the rate at which the cigarettes Z are transported through the two testing stations. The output of the AND-gate 98a is connected with one input of an OR-gate 97.

The setting of the threshold circuit 92a is such that its output transmits a signal when the pressure of fluid in the pipe 82a (and hence in the major portion of the wrapper of the cigarette Z advancing through the testing device 71a) is below a predetermined minimum value (selected by setting of the source 94a of reference signals), i.e., when the permeability of the wrapper of the plain cigarette T forming part of that cigarette Z which advances through the testing device 71a is excessive.

As mentioned above, the construction of the measuring or evaluating circuit 86b is identical with that of the circuit 86a except that the output of the threshold circuit 92b transmits a signal when the permeability of the wrapper of the filter mouthpiece F advancing through the testing device 71b is less than a predetermined minimum acceptable value selected by the setting of an adjustable source 94b of reference signals. The right-hand input of the AND-gate 98b is connected with the proximity switch 99a, and the output of the gate 98b is connected with a second input of the OR-gate 97.

The pressure gauges 84a and 84b detect changes in the permeability of wrappers of successive plain cigarettes T and filter mouthpieces F. Due to their inertia, these gauges can be said to constitute means for integrating a plurality of successive pressure signals (i.e., for integrating all signals which are generated within preselected intervals of time) and for indicating changes of the intensity of integrated signals. The inertia of gauges 84a and 84b constitutes a time constant so that, when the conveyor 31 is driven at a given speed (i.e., when the filter cigarette making machine turns out a given number of cigarettes Z per unit of time), the indications furnished by pointers of the gauges 84a and 84b respectively denote the average permeability of the wrappers of plain cigarettes T and the average permeability of predetermined portions of the wrappers of filter mouthpieces F.

The output of the OR-gate 97 is connected to the first stage of a shift register 101 which receives signal-transporting pulses from the proximity switch 99a and whose output is connected with a solenoid-operated valve 104 by way of an amplifier 103. The valve 104 is normally closed and is installed in a conduit 108 connecting a source 106 of compressed gas (e.g., air) with an ejector nozzle 107 which is adjacent to the path of cigarettes Z on the conveyor 32 of FIG. 1 and discharges a jet of compressed gas against an oncoming defective cigarette Z whenever the one or the other input of the OR-gate 97 receives a signal (from the measuring or evaluating circuit 86a or 86b). The parts 103, 104, 106, 107, 108 together constitute an automatic segregating or ejecting device 102 which effects the separation of defective cigarettes Z from satisfactory cigarettes and thus insures that defective cigarettes cannot be transferred onto the upper reach of the belt conveyor 36.

If desired, the conveyor 32 can be associated with a testing device which is located ahead of the segregating or ejecting station for defective cigarettes and serves to ascertain the density of tobacco-containing ends of cigarettes Z. Cigarettes wherein the density of tobacco-containing ends is unsatisfactory can be ejected at the segregating station for cigarettes having defective wrappers.

The operation:

When a recess 46 of the conveyor 31 reaches and travels along the concave inner side of the shroud 48, its compartment 46a communicates with the suction intake of the blower 76 (via pipe 87, branch 87a, space 52a, slot 53a and channel 54a) before the compartment 46b of the same recess 46 begins to communicate with the suction intake of the blower 76 (via pipe 87, branch 87b, space 52b, slot 53b and channel 54b). In fact, the compartment 46a of a recess 46 is already sealed from the pipe 87 when the latter begins to communicate with the compartment 46b of the same recess 46. The channel 54a draws air from the respective compartment 46a at a rate which is a function of permeability of the major portion of or the entire wrapper of the respective cigarette Z. The compartment 46a draws atmospheric air into the pipe 82a and groove 62 of the valve plate 61 at a rate which depends mainly or practically exclusively on permeability of the wrapper of the plain cigarette T. The output of the transducer 91a transmits an electrical signal whose intensity or another characteristic is indicative of pressure in the pipe 82a. The threshold circuit 92a compares such signal with the reference signal (from the source 94a) and transmits a signal to the AND-gate 98a when the intensity of signal at the output of the transducer 91a is indicative of unsatisfactory permeability of the wrapper of the tested plain cigarette T, namely, when the permeability of the wrapper is excessive because the wrapper has an open seam, a relatively large hole or another defect which warrants segregation of the corresponding cigarette Z from other (satisfactory) cigarettes. The other input of the gate 98a simultaneously receives a signal from the proximity switch 99a so that the output of the gate 98a transmits a signal to the corresponding input of the OR-gate 97 whose output transmits a signal to the first stage of the shift register 101. The pulse generator 99 causes the shift register 101 to transport such signal toward the amplifier 103 at a speed corresponding to the speed of travel of detected defective cigarette Z to the ejecting station (device 102) at, in or on the conveyor 32. The rate at which the pulse generator 99 causes its proximity switch 99a to transmit pulses to the AND-gates 98a, 98b corresponds to the rate at which the holes 57 of the flange 56 of the conveyor 31 move into register with the groove 62 of the valve plate 61.

When a compartment 46b communicates with the pipe 87, it draws air (via pipe 82b and the wrapper of the filter mouthpiece F therein) at a rate which is indicative of permeability of the wrapper of the mouthpiece. Such permeability is attributable (either mainly or exclusively) to the provision of holes or perforations L in the tube B surrounding the mouthpiece F which advances through the testing device 71b. The output of the transducer 91b transmits electrical signals whose intensity or another characteristic is indicative of permeability of successive mouthpieces. The threshold circuit 92b compares such signals with the reference signal which is furnished by the source 94b, and the output of the circuit 92b transmits a signal to the corresponding input of the AND-gate 98b when the permeability of the tested mouthpiece wrapper is too low, for example, because the perforating device has failed to provide the mouthpiece wrapper B with a requisite number of holes L or because the diameters of such holes are too small. The cigarette Z wherein the wrapper of the mouthpiece F is defective (because its permeability is too low) is thereupon segregated from satisfactory cigarettes Z in the same way as described above in connection with cigrettes which are defective because the permeability of their plain cigarette wrappers is excessive. Thus, the output of the AND-gate 98b transmits a signal to the OR-gate 97 which transmits the signal to the first stage of the shift register 101 and the latter transports the signal on to the amplifier 103 which causes the device 102 to eject the respective cigarette Z from the conveyor 32. The gauge 84a furnishes readings denoting the average permeability of the wrappers of a series of successive plain cigarettes T, and the gauge 84b furnishes readings denoting the average permeability of the wrappers of a series of successive filter mouthpieces F. A person observing the pointers of the gauges 84a and 84b of reference signals for the respective threshold circuits 92a, 92b. As mentioned above, the permeability of the wrappers of filter mouthpieces F is attributable (either primarily or exclusively) to the provision of holes L. Also, the maximum sensitivity of testing device 71b is in the region of holes L (see FIG. 2).

The measuring or evaluating circuits 86a and 86b insure that none of the defective cigarettes Z can reach the belt conveyor 36. Thus, the segregating device 102 ejects each cigarette Z which exhibits excessive permeability in the region of the wrapper of its plain cigarette T and/or insufficient permeability in the region of the wrapper of its filter mouthpiece F. It is clear that the apparatus of FIGS. 1 to 4 can be provided with two discrete segregating devices one of which ejects defective cigarettes detected by the testing device 71a and the other of which ejects defective cigarettes detected by the testing device 71b.

A modification of the just described testing apparatus is shown in FIG. 4 by a phantom line PL. Thus, the branch 88a of the suction pipe 87 can be connected with successive compartments 46a as well as with the registering compartments 46b. Consequently, the device 71a can test the wrappers of entire cigarettes Z while the interior of such cigarettes communicates with the groove 62 of the valve plate 61. Such modification insures that the device 102 segregates cigarettes Z whose wrappers are defective in the regions of the plain cigarettes T (e.g., due to open seams and/or the presence of relatively large holes) and/or cigarettes whose wrappers are defective in the regions of the filter mouthpieces F (for example, because the combined permeability of the wrappers of a plain cigarette and the adjacent mouthpiece is excessive due to a defect of the wrapper of the plain cigarette and/or due to excessive combined cross sectional area of holes L in the wrapper of the mouthpiece).

It is further within the purview of the invention to equip the apparatus with two testing devices which do not have any common parts or wherein the number of common parts is less than in the apparatus of FIGS. 1-4. For example, the first testing device (71a or 71b) can be associated with the conveyor 28 of the turn-around device 29 and the second testing device (71b or 71a) can be associated with the conveyor 31. The measuring or evaluating circuits of both testing devices can transmit signals to a common segregating device or to two discrete segregating devices.

Figures 5, 6:
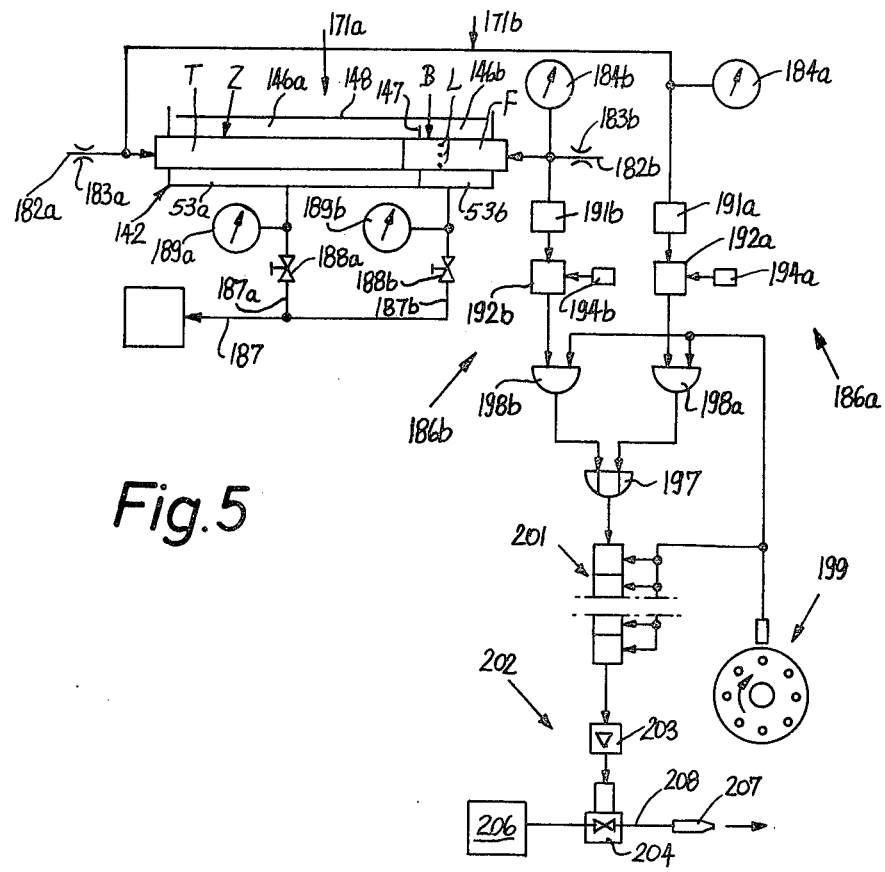
FIG. 5 is a similar diagrammatic view of a modified testing apparatus wherein the major portions of the wrappers are tested simultaneously with the perforated wrapper portions.
FIG. 6 is a diagrammatic view of still another testing apparatus which does not or need not have means for segregating articles having unsatisfactory perforated wrapper portions from other articles.

FIG. 5 shows another testing apparatus wherein testing of the wrapper of the plain cigarette T of each cigarette Z takes place simultaneously with testing of the wrapper of the respective filter mouthpiece F, i.e., the two testing devices or units are adjacent to one and the same portion of the path along which the cigarettes move sideways. All such parts of this testing apparatus which are identical with or clearly analogous to corresponding parts of the apparatus of FIG. 4 are denoted by similar reference characters plus 100. The groove 62 in the valve plate 61 (not shown) of the testing apparatus of FIG. 5 is in register with the groove 69 of the valve plate 68 (not shown). Also, the slot 53a is in register with the slot 53b of the shaft 37 (not shown in FIG. 5). In all other respects, the construction of the testing apparatus of FIG. 5 is identical with the construction of the apparatus of FIG. 4. Also, its operation is identical to that of the apparatus of FIG. 4, except that the OR-gate 197 can receive a signal from the AND-gate 198a simultaneously with a signal from the AND-gate 198b, i.e., in certain instances when the wrappers of cigarettes Z are defective in the region of their plain cigarettes T as well as in the region of their filter mouthpieces F, a single signal (from the output of the gate 197) will suffice to effect segregation of such cigarettes from satisfactory cigarettes Z.

FIG. 6 shows a further testing apparatus wherein the testing devices or units 271a and 271b test the wrappers of successive filter cigarettes Z in different portions of the path of sidewise movement of such cigarettes and wherein the mode of testing by the device 271a is different from the mode of testing by the device 271b. The device 271a tests the cigarettes Z by causing a testing fluid to flow into one and toward and beyond the other end of the wrapper, and the device 271b tests successive cigarettes Z by admitting testing fluid to both ends of the respective wrappers. Thus, the mode of operation of the device 271a can be said to constitute a blow-through method whereas the operation of the device 271b can be termed a blow-up method.

The testing conveyor which is used in combination with the testing devices 271a, 271b of FIG. 6 is modified in that the valve plate 61 (not shown in FIG. 6) comprises two discrete grooves 62 (disposed one behind the other, as considered in the direction of rotation of the conveyor and disk 299c of the pulse generator 299) and the valve plate 68 (not shown in FIG. 6) also comprises two discrete grooves 69 disposed one behind the other so that each groove 62 is in register with a groove 69 (as considered in parallelism with the axis of the conveyor). The first testing station (device or unit 271a) is located between the upstream grooves 62, 69 and the second testing station (device or unit 271b) is located between the downstream grooves 62, 69 or vice versa.

The testing device 271a comprises a branch pipe 287a which is connected with a pipe 287 communicating with the pressure outlet of a blower 276 or another suitable source of compressed air or another testing fluid. The branch pipe 287a contains a pressure regulating valve 288a and a high-inertia pressure gauge 289a and is connected with the upstream groove 62 of the valve plate 61. The branch pipe 287a further contains a preferably adjustable flow restrictor 281a downstream of the valve 288a. The testing fluid which is admitted via branch pipe 287a enters the left-hand end of the wrapper of the cigarette Z between the upstream grooves 62, 69 and flows axially through such wrapper to issue from the other end which communicates with a pipe 282a containing a pressure gauge 284a and a preferably adjustable flow restrictor 283a. The pipe 282a is further connected to the transducer 291a of a measuring or evaluating circuit 286a whose construction is analogous to that of the measuring circuit 86a. Therefore, the parts of the circuit 286a are designated by the same reference characters as those used in FIG. 4 plus 200. The output of the threshold circuit 292a transmits a signal when the intensity of electrical signal furnished by the transducer 291a is indicative of excessive permeability of the wrapper of that cigarette Z whose wrapper communicates with the pipes 287a and 282a.

The right-hand input of the AND-gate 298a of the measuring or evaluating circuit 286a is connected with the proximity switch 299a of the pulse generator 299 whose disk 299c rotates in synchronism with the conveyor serving to transport cigarettes Z past the two testing stations. If both inputs of the gate 298a receive signals at the same time, the output of this gate transmits a signal to the first stage of a shift register 301 which receives pulses from the proximity switch 299a and transports the incoming signals in simulation of movement of a defective cigarette Z toward the ejecting station where the defective cigarette is segregated from satisfactory cigarettes by the device 302 including a source 306 of compressed air, and ejector nozzle 307, a normally closed solenoid-operated valve 304 in the conduit 308 and an amplifier 303 between the output of the shift register 301 and the valve 304. It is clear that that shift register 101, 201 or 301 can be replaced by another suitable time-delay unit, as long as such unit is capable of delaying the segregation of defective cigarettes until the cigarettes arrive at the ejecting station. The nozzle 307 can be placed adjacent to the path of movement of cigarettes in the flutes of the conveyor 32 shown in FIG. 1.

The second testing device 271b comprises a second branch pipe 287b which forms part of the pipe 287 and includes branches 287b', 287b" serving to admit pressurized testing fluid into opposite ends of the wrapper of a cigarette Z moving through the second testing station between the downstream grooves 62 and 69. The branch 287b contains a pressure regulating valve 288b and a preferably adjustable flow restrictor 281b. The branch 287b" contains a further preferably adjustable flow restrictor 285b and a pressure gauge 284b. The gauge 284b can be said to constitute a means (286b) for monitoring or measuring the pressure of testing fluid which is admitted into the wrapper of the cigarette Z at the second testing station and for indicating the presence or absence of cigarettes wherein the wrappers of filter mouthpieces F exhibit or are likely to exhibit unsatisfactory permeability (namely, insufficient permeability most likely to be caused by improper operation or adjustment of the perforating device or devices). The inertia of the gauge 284a is preferably high so that the position of its pointer indicates the average permeability of a series of successive wrappers. The gauge 284b may be identical with the gauge 84a or 84b of FIG. 4. The inertia of this gauge constitutes a time constant so that, when the filter cigarette making machine is operated at a given speed, the pointer of this gauge invariably indicates the condition (average permeability) of a given number of predetermined portions of successively tested wrappers.

It is clear that the gauge 284b can be replaced with a second monitoring or evaluating circuit which is similar to the circuit 86b of FIG. 4 and whose AND-gate transmits signals to the input of the shift register 301 or directly to the valve 304, always in synchronism with operation of the pulse generator 299.

The flow restrictor 285b in the branch 287b" insures that one part of the testing device 271b is more sensitive than the other part, i.e., that the device 271b can determine, with a high degree of accuracy, the permeability of those (predetermined) portions of wrappers of successive cigarettes Z which surround the respective filter mouthpieces F. In other words, eventual fluctuations of permeability which are indicated by the pointer of the gauge 284b are attributable, either primarily or exclusively, to deviations of the combined cross-sectional area of holes L from a desired value.

The testing device 271a determines the permeability of the entire wrapper of each cigarette Z, i.e., the apparatus of FIG. 6 invariably segregates all such cigarettes whose wrappers are clearly defective. If desired, the gauge 284a can be combined with or replaced by a device which automatically adjusts the perforating device when the position of the pointer of this gauge is indicative of unsatisfactory (especially insufficient) permeability of filter mouthpiece wrappers, i.e., when the combined cross-sectional area of holes L is less than necessary for admission of requisite quantities of atmospheric air into the column of tobacco smoke.

If the apparatus of FIG. 6 comprises a discrete drum-shaped conveyor for each of the testing devices 271a and 271b, such modified apparatus can be equipped with suitably configurated and controlled flaps or baffles (e.g., flaps of the type disclosed in commonly owned U.S. Pat. No. 3,339,402 granted Sept. 5, 1967 to W. Rudszinat) which can be actuated to mechanically confine those portions of cigarette wrappers which should not be tested by the device 271a and/or 271b. For example, the baffle or baffles which are associated with the drum-shaped conveyor of the testing device 271a can seal the holes L so that the device 271a tests the entire wrapper of each cigarette save for the perforated portion. The baffle or baffles which are associated with the drum-shaped conveyor of the testing device 271b then confine the entire wrapper of each cigarette save for the portion which is provided with the holes L so that the device 271b serves exclusively to determine the permeability of perforated portions of successive cigarettes.

The testing apparatus of FIG. 6 will be utilized when it suffices to detect the trend or drift of deviations of permeability of predetermined (perforated) wrapper portions from a desired optimum permeability. Thus, the position of the pointer of the gauge 284b will indicate, at least to a reasonably skilled attendant, whether or not the permeability of perforated portions drifts in a direction above or below the desired optimum permeability which can be designated by a graduation on the scale of the gauge 284b. On the other hand, the testing apparatus of FIGS. 1-4 and 5 can furnish the information which is supplied by the gauge 284b (see the gauges 84b and 184b) as well as signals (at the outputs of the threshold circuits 92b, 192) which denote the exact magnitude of positive or negative deviations of permeability of predetermined wrapper portions from the minimum acceptable permeability (as selected by the setting of sources 94b and 194b).

The integrating action of the gauges 84b, 184b and 284b can be selected in such a way that these gauges furnish readings denoting the average permeability of a fixed number of predetermined wrapper portions or the average permeability of those predetermined wrapper portions which are tested per unit of time. The number of predetermined wrapper portions is the same in both instances if the conveyor 31 is driven at a constant speed.

It is further clear that the testing device 71b, 171b or 271b can be modified so that it can furnish indications or discrete signals denoting those articles Z wherein the permeability of predetermined wrapper portions (namely, of those wrapper portions which are provided with holes L) is less than a minimum permissible permeability or in excess of a maximum permissible permeability. However, it has been found that it often suffices to detect those articles wherein the permeability of predetermined wrapper portions is less than a minimum permissible permeability because predetermined wrapper portions of excessive permeability can be detected by the device 71a, 171a or 271a.

FIG. 6 further shows that the testing of wrappers by the device 271a can involve an examination of entire wrappers inclusive of the predetermined (perforated) wrapper portions. The same applies for the embodiment which has been described in connection with FIG. 4 (see the phantom line PL). In the embodiment of FIG. 5, the testing by device 171a involves, either primarily or exclusively, an examination of the condition of a major portion of the wrapper (including the entire wrapper of the plain cigarette T and a small portion of the tube B), and the testing by device 171b involves an examination of the condition of a relatively small (in fact, minute) portion of the entire wrapper (namely, of that portion of the wrapper which is formed with the holes L). In other words, the range of the testing device 171a is limited to a relatively large part of the wrapper which does not include the portion with holes L, and the range of the testing device 171b is limited, exclusively or practically exclusively, to that part of the wrapper which is formed with the holes L. The operation of the testing apparatus of FIG. 5 is highly reliable because the examination of predetermined (perforated) wrapper portions is not influenced by eventual defects of other portions of the wrappers (such other portions are adequately monitored by the testing device 171a).

The heretofore described testing apparatus can be used to ascertain trends in the changes of permeability of selected (intentionally perforated) portions of the wrappers of successive cigarettes. Such trends are or can be ascertained by resorting to relatively simple and reliable testing apparatus which can employ a large number of components corresponding to those used in certain presently known testing apparatus which are reliable in operation and are forced by the manufacturers of rod-shaped smokers' products.

Figure 9:
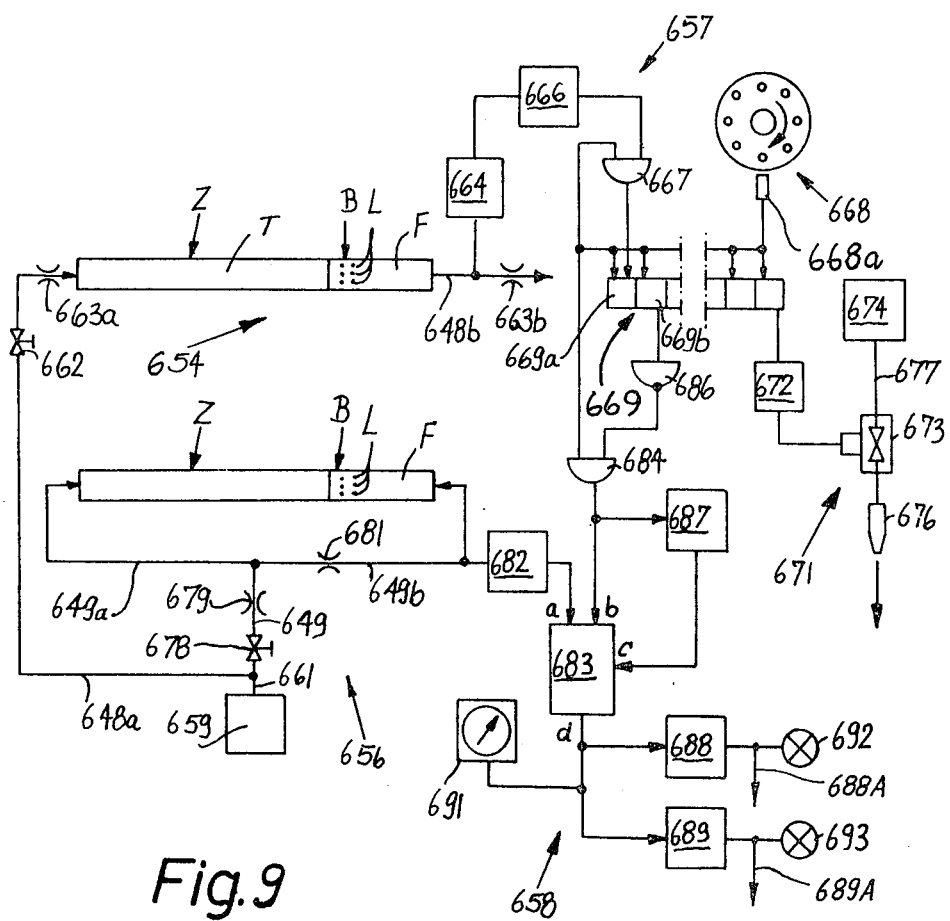
FIG. 9 is a diagrammatic view of a testing apparatus which includes the conveyor of FIGS. 7 and 8.
Figure 10:
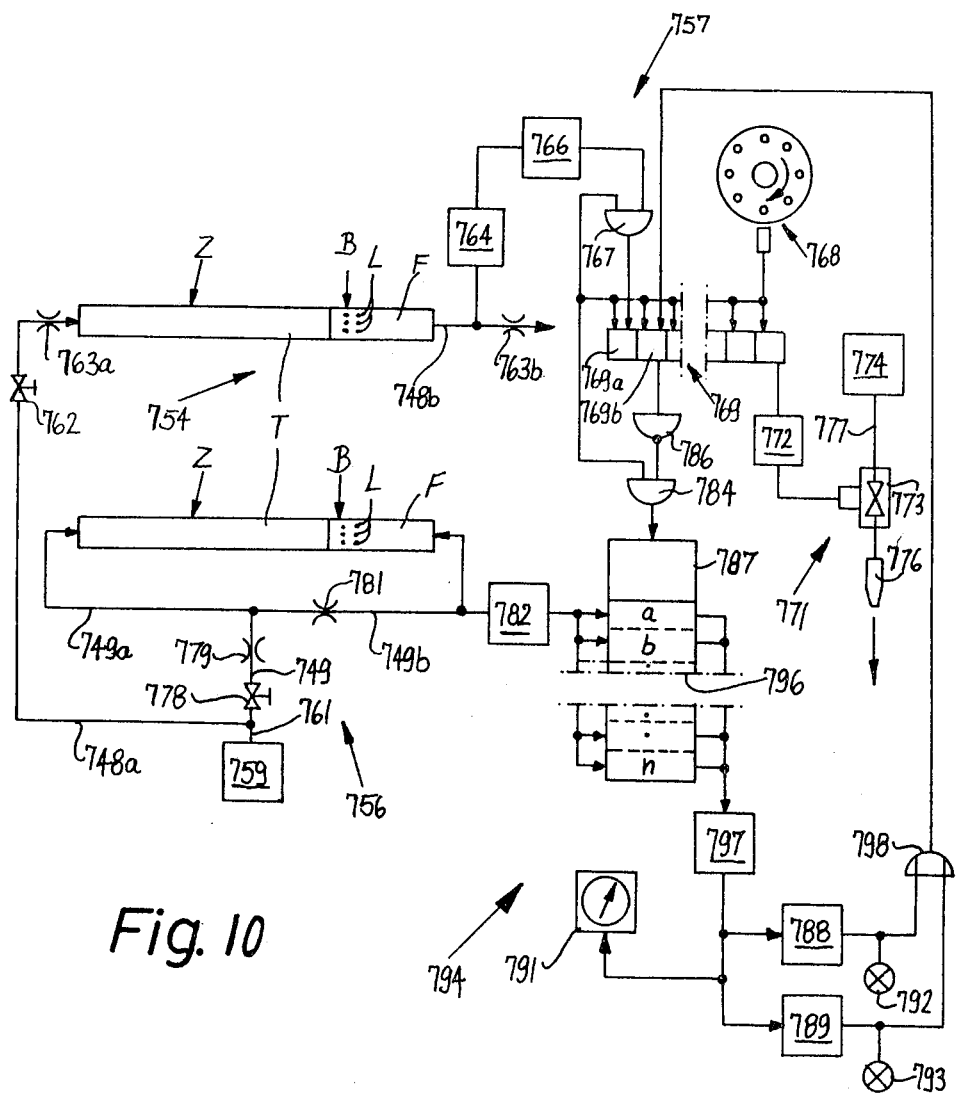
FIG. 10 is a diagrammatic view of a testing apparatus which constitutes a modification of the apparatus of FIG. 9.

The apparatus which are shown in FIGS. 9 and 10 serve for even more accurate determination of such trends, namely, for determination of trends with a degree of accuracy which is sufficiently high to warrant the use of signals denoting the permeability of selected wrapper portions (especially those which are provided with intentionally formed holes) for regulation of the perforating unit or units.

Referring again to FIG. 1, the reference character 615 denotes a perforating unit which is installed in the machine of FIG. 1 to form holes or perforations L in the web 13 immediately ahead of the paster 18. If the filter cigarette making machine of FIG. 1 embodies the perforating unit 615, the paster 18 is constructed in such a way that the row or rows of holes L formed by unit 615 are not coated with adhesive. The perforating unit 615 may be of the type disclosed in the aforementioned copending application Ser. No. 841,108 of Wahle et al. It comprises spark generating means which is preferably designed to provide the web 13 with several rows of small holes L. The perforating unit 615 is adjustable, either by hand or automatically, so as to change the size of each hole L and/or the number of holes per unit length of the web 13.

Referring to FIGS. 7 and 8, there is shown a portion of a testing conveyor 631 which can be used as a substitute for the conveyor 31 of FIGS. 1-3 and forms part of a modified testing apparatus. This testing apparatus is a modification of the apparatus shown in FIGS. 4, 5 and 6. A testing apparatus which can be utilized for the practice of the present invention and which employs a conveyor similar to the conveyor 631 of FIGS. 7 and 8 is also disclosed in the aforementioned commonly owned U.S. Pat. No. 3,948,084 to Heitmann et al. In fact, the testing apparatus of Heitmann et al. can be readily converted into a testing apparatus of the type shown in FIGS. 7 to 9. Therefore, FIGS. 7 and 8 merely shown certain parts of the conveyor 631 because several illustrated parts and practically all other parts which are necessary for proper operation of the conveyor 631 are either similar to or identical with the corresponding parts of the patented testing apparatus. The patent to Heitmann et al. is incorporated herein by reference.

The conveyor 631 is driven to rotate in the direction indicated by arrow 653. It comprises a drum-shaped body 637 with a circumferential groove 638 between two flanges 651a and 651b. The periphery of the body 637 is provided with pairs of aligned U-shaped projections or cradles 639 which define article-receiving flutes communicating with radially inwardly extending suction ports 641. When two aligned flutes receive a filter cigarette Z from the conveyor 28 of FIG. 1, the cigarette is attracted to the respective cradles 639 during travel from the transfer station between the conveyors 28, 631 to the transfer station between the conveyors 631, 32. The manner in which the suction ports 641 communicate with a suction generating device during travel of the respective cradles 639 from the conveyor 28 to the conveyor 32 is preferably the same as disclosed in U.S. Pat. No. 3,948,084. Thus, the ports 641 can be communicatively connected with the suction generating device by a stationary valve plate which lies against one end face of the body 637 radially inwardly of the respective flange 651a or 651b and has an arcuate groove which is connected to the inlet of the suction generating device.

The flanges 651a, 651b are inwardly adjacent to stationary annular valve plates 644a, 644b each of which has two arcuate grooves 642a, 643a and 642b, 643b machined into that side which is adjacent to the respective flange. The groove 642a receives compressed testing fluid (e.g., air) from a pipe 648a, and the groove 642b discharges testing fluid into a pipe 648b. The grooves 643a, 643b receive compressed testing fluid from pipes 649a, 649b.

The width of the circumferential groove 638, as considered in the axial direction of the drum-shaped body 637, exceeds the length of a filter cigarette Z. The cigarettes Z which are delivered by successive flutes of the conveyor 28 of FIG. 1 enter the groove 638 in such a way that their tobacco-containing ends are adjacent to the flange 651a and their filter mouthpieces F are nearer to the flange 651b. The latter carries axially movable sealing elements or nipples 646, one for each pair of cradles 639 and each movable axially toward and away from the flange 651a. The nipples 646 are biased in a direction to the left, as viewed in FIGS. 7 and 8, by helical springs 647 and can be shifted against the resistance of such springs by suitable cam means in a manner as disclosed in U.S. Pat. No. 3,948,084. The cam means retracts successive nipples 646 at the transfer station between the conveyors 28, 631 as well as at the transfer station between the conveyors 631, 32 so as to allow for unimpeded transfer of cigarettes Z onto and off the conveyor 631. A cigarette Z which is properly received in the flutes of two aligned cradles 639 is biased by the respctive nipple 646 so that its tobacco-containing end bears against the flange 651a and the left-hand end of the tubular wrapper of such cigarette registers with a bore or hole 652a of the flange 651a. At the same time, the right-hand end of the wrapper of the same cigarette Z communicates with a bore or hole 652b in the right-hand flange 651b via axial bore in the corresponding nipple 646. The bores 652a and 652b respectively travel past the grooves 642a, 643a and 642b, 643b.

The length of the groove 642a, (as considered in the circumferential direction of the conveyor 631) equals or approximates the distance between the axes of two neighboring bores 652a or 652b, and the length of each of the grooves 652a, 653a and 653b is approximately one-half the length of the groove 652a. As shown in FIG. 8, the groove 642a will admit compressed testing fluid into the left-hand ends of the wrappers of successive cigarettes Z which travel between the valve plates 644a, 644b (in the direction indicated by arrow 653) whereby the testing fluid flows axially into the wrappers and is discharged into the pipe 648b via corresponding nipple 646, registering bore 652b and groove 642b when the right-hand end of the same wrapper begins to communicate with the groove 642b. The testing fluid which enters the wrapper before the respective cigarette Z reaches the groove 642b exerts pressure against the interior of the wrapper, i.e., the latter is "blown up." It will be noted that the groove 642b is aligned with the downstream half of the groove 642a, as considered in the direction indicated by arrow 653. If the wrapper which travels past the groove 642a has a pronounced leak, the pressure of testing fluid which flows into the groove 642b and pipe 648b (when the respective cigarette reaches the groove 642b) is well below that pressure which is indicative of an acceptable wrapper.

The length of the grooves 643a, 643b is preferably identical and these grooves are in exact alinement with each other, i.e., one end of a wrapper reaches the groove 643a at the same time when the other end of the same wrapper reaches the groove 643b. Both grooves admit compressed testing fluid so that the wrapper therebetween is also "blown up" and remains in such condition during travel between the grooves 643a, 643b.

The holes which are formed by the perforating unit 615 of FIG. 1 are shown at L. These holes form two annuli and are provided in the uniting band B which is converted into a tube sealingly connecting the plain cigarette T with the filter mouthpiece F of the respective filter cigarette Z.

The pipes 648a, 648b form part of a first testing device or unit 654 which examines the entire wrapper of each cigarette Z at the testing station including the grooves 642a, 642b. A second testing device or unit 656 examines the entire wrappers of successive cigarettes Z at a second testing station including the grooves 643a, 643b. The second testing device 656 includes the pipes 649a, 649b. As shown in FIG. 9, the testing devices 654, 656 comprise two discrete evaluating or measuring circuits 657, 658 and the evaluating circuit 657 transmits signals to an ejecting or segregating device 671.

The pipe 648a of the testing unit 654 receives compressed testing fluid from a source 659 whose outlet is connected with a main pipe 661. The latter communicates with the pipe 648a. The pipe 648a contains a pressure regulating valve 662 and a preferably adjustable flow restrictor 663a located ahead of the groove 642a in the valve plate 644a (not shown in FIG. 9). The pipe 648b communicates with the atmosphere and contains a preferably adjustable flow restrictor 663b upstream of a branch pipe which admits testing fluid to a transducer 664 of the evaluating circuit 657. The transducer 666 converts pneumatic signals into electrical signals and transmits electrical signals to a threshold circuit 666 whose output is connected with one input of an AND-gate 667. The threshold circuit 666 transmits a signal only if the pressure of testing fluid in the pipe 648b is below a predetermined minimum pressure denoting a still satisfactory wrapper. In other words, the threshold circuit 666 transmits a signal only when the permeability of the wrapper between the grooves 642a, 642b is excessive.

The other input of the AND-gate 667 is connected to a proximity switch 668a forming part of a pulse generator 668 which generates pulses at the frequency at which the cigarettes Z advance past the two testing stations. When the two inputs of the AND-gate 667 receive signals at the same time, the output of the gate 667 transmits a "defect" signal to the first stage 669a of a shift register 669 whose stages receive signal transporting pulses from the pulse generator 668. The "defect" signal advances through the shift register 669 at the same rate at which the corresponding cigarette Z (having a defective wrapper) advances toward the conveyor 32 of FIG. 1, namely, toward the segregating device 671 which is mounted on, in or adjacent to the conveyor 32. The pulse generator 668 is driven in synchronism with the testing conveyor 631.

The segregating device 671 comprises a source 674 of compressed gas (preferably air) which is connected with a conduit 677 containing a solenoid-operated valve 673 and serving to admit compressed air to an ejector nozzle 676 when the valve 673 is open. The nozzle 676 can expel defective cigarettes Z from a selected flute of the conveyor 32. The signals for energization of the solenoid of the valve 673 are transmitted by the last stage of the shift register 669 via amplifier 672.

The pipes 649a, 649b of the testing device 656 receive compressed testing fluid from the aforementioned pipe 661 via pipe 649 which contains a pressure regulating valve 678 and a preferably adjustable flow restrictor 679. The pipe 649b contains a preferably adjustable flow restrictor 681 which insures that the sensitivity of the right-hand half of the testing device 656 (as viewed in FIG. 9) exceeds the sensitivity of the left-hand half, i.e., the testing device 656 monitors the permeability of the convoluted uniting bands B with a higher degree of accuracy than the permeability of the wrappers of plain cigarettes T.

A transducer 682 of the evaluating circuit 658 receives compressed testing fluid from the pipe 649b intermediate the flow restrictor 681 and the groove 643b (not shown in FIG. 9). Since the sensitivity of the testing unit 656 is asymmetric, the transducer 682 transmits electrical signals whose characteristics denote primarily the permeability of the convoluted uniting band B at the testing station including the grooves 643a, 643b. In other words, electrical signals which are transmitted by the transducer 682 denote primarily the permeability of that wrapper portion which is formed with the holes L.

The output of the transducer 682 is connected with the input a of an averaging circuit 683. A second input b of the circuit 683 is connected with the output of an AND-gate 684 one input of which is connected with the proximity switch 668a and the other input of which is connected with the second stage 669b of the shift register 669 by way of a NO-gate or inverter 686. The gate 686 is connected with the second stage 669b because the distance between the two testing stations of FIG. 9 equals the distance between two neighboring cigarettes Z on the conveyor 631. A third input c of the averaging circuit 683 is connected with a counter 687 whose input receives signals from the output of the AND-gate 684. The construction of the averaging circuit 683 is such that its input a accepts a signal only when the input b receives a signal from the output of the AND-gate 684, i.e., when the stage 669b of the shift register 669 does not store a "defect" signal. The output d of the averaging circuit 683 transmits a signal in response to reception of a signal at the input c (from the counter 687). A signal which is transmitted to the input c simultaneously resets the circuit 683 to zero. The signal which is transmitted by the output d of the averaging circuit 683 denotes the average permeability of a group consisting of a predetermined number of successive uniting bands B (the number is selected by the setting of the counter 687).

The output d of the averaging circuit 683 transmits signals to a gauge 691 and to two threshold circuits 688, 689. The pointer of the gauge 691 furnishes visible indications of average permeability of a group consisting of a predetermined number of uniting bands B. The threshold circuit 688 transmits a signal to a lamp 692 when the average permeability of a series of successive uniting bands B is less than a predetermined minimum acceptable value, and the threshold circuit 689 transmits a signal to a second lamp 693 when the average permeability of a predetermined number of successively tested uniting bands B exceeds the maximum permissible permeability. It can be said that the signals furnished by the lamps 692, 693 resectively denote that the combined cross-sectional area of holes L in a series of uniting bands B is too small and excessive.

The operation of the apparatus of FIG. 9 is as follows:

As a cigarette Z approaches the first testing station, one end of its wrapper receives compressed testing fluid from the groove 642a and such fluid thereupon passes into the pipe 648b when the right-hand end of the same wrapper communicates with the groove 642b. The circuit 657 evaluates the permeability of the entire wrapper. If a wrapper exhibits a pronounced leak, e.g., because its seam is open, the pressure of fluid in the pipe 648b is low and the signal which is transmitted by the transducer 664 is indicative of a defective cigarette. As mentioned above, such signal is transmitted to the corresponding input of the AND-gate 667 via threshold circuit 666. The pulse generator 668 insures accurate timing of transmission of the "defect" signal to the first stage 669a of the shift register 669. The "defect" signal is propagated through the shift register 669 at the same speed at which the defective cigarette Z advances toward the ejecting station, e.g., into the range of the ejector nozzle 676. When the defective cigarette reaches the ejecting station, the last stage of the shift register 669 transmits the "defect" signal to the amplifier 672 of the segregating unit 671 and the amplifier energizes the coil of the solenoid of the valve 673 which opens for a minute fraction of a second and enables a stream of compressed gas to flow from the source 674 into the ejector nozzle 676 via conduit 677. The ejected defective cigarette is intercepted in a receptacle, not shown.

A cigarette Z which has been tested at the first station including the grooves 642a, 642b thereupon advances into the space between the grooves 643a, 643b and the pipes 649a, 649b admit compressed testing fluid to both ends of the respective wrapper. Due to asymmetric operation of the testing unit 656, the intensity of pneumatic signal which is transmitted to the transducer 682 of the evaluating circuit 658 depends primarily on the combined cross-sectional area of holes L in the wrapper between the grooves 643a, 643b. The transducer 682 transmits a corresponding electrical signal to the input a of the averaging circuit 683. However, the circuit 683 accepts such a signal only if its input b receives a signal from the second stage 669b of the shift register 669 via inverter 686 and AND-gate 684. The transmission of signal to the input b of the averaging circuit 683 is timed (by pulse generator 668 via AND-gate 684) in such a way that the input b receives a signal which denotes the condition of the corresponding wrapper (as determined by the first evaluating circuit 657) simultaneously with transmission to the input a of a signal denoting the permeability of the convoluted uniting band B of the same wrapper. The inverter 686 insures that the input b of the averaging circuit 683 receives a signal only when the corresponding wrapper is satisfactory, i.e., when the testing unit 654 and the associated evaluating circuit 657 determine that the permeability of the wrapper, as a whole, is within the acceptable range. It will be seen that the circuit 683 averages only those signals which are obtained on testing of bands B forming part of wrappers which were found to be satisfactory during travel through the first testing station.

The counter 687 receives a signal only when the output of the AND-gate 684 transmits a signal to the input b of the averaging circuit 683. Thus, the counter 687 counts only those bands B which form part of wrappers whose permeability is acceptable to the evaluating circuit 657. When the number of signals which are transmitted to the input b of the averaging circuit 683 reaches a preselected value, the output of the counter 687 transmits a signal to the input c of the circuit 683 whereby the output d of the circuit 683 transmits a signal to the gauge 691 and threshold circuits 688, 689. The intensity of the signal at the output d of the circuit 683 denotes the average permeability of a predetermined number of successive bands B forming part of wrappers which are acceptable to the evaluating circuit 657, i.e., which failed to cause the generation of a "defect" signal. At the same time, the signal which is transmitted by the counter 687 resets the averaging circuit 683 to zero so that the latter can begin with accumulation and averaging of a fresh series of signals.

An attendant who observes the pointer of the gauge 691 can ascertain the average permeability of the predetermined number of bands B and, if necessary, adjusts the perforating unit 615 to increase or reduce the combined cross-sectional area of holes L per unit length of the web 13. The threshold circuit 688 or 689 causes the corresponding lamp 692 or 693 to transmit a visible signal when the average permeability of the selected number of freshly tested bands B is too low or excessive. This enables an attendant to determine whether or not the perforating unit 615 requires adjustment even though the attendant is not standing or sitting next to the gauge 691.

It is clear that the signals which are transmitted by the threshold circuits 688, 689 can be transmitted directly to the controls of the perforating unit 615, i.e., that the latter can be adjusted automatically whenever the evaluating circuit 658 ascertains that the average permeability of a series of successive bands B is outside of an acceptable range. The operative connections between the circuits 688, 689 and unit 615 are respectively shown at 688A and 689A. These operative connections cause the perforating unit 615 to alter the combined cross-sectional area of holes L per unit length of the web 13, preferably by changing the number of holes.

The reason for elimination from the averaging of permeabilities of uniting bands B of each and every band which forms part of a wrapper whose permeability is too high (as determined by the monitoring circuit 657) is that the wrapper whose permeability is too high would unduly distort the signals which are transmitted by the threshold circuit 688, i.e., of those averaged signals which denote that the permeability of a predetermined number of successively tested uniting bands B is too low. Consequently, the characteristics of each signal which is transmitted by the averaging circuit 683 accurately reflect the average permeability of a given number of uniting bands B which form part of acceptable wrappers (as determined by the testing device 654 and its measuring circuit 657). The averaging operation is highly reliable regardless of the number of signals (furnished by the transducer 682) which are averaged by the circuit 683. However, the accuracy of such signals is even higher if the number of signals which the input a of the averaging circuit 683 receives prior to transmitting a signal to the gauge 691 and threshold circuits 688, 689 is always the same.

FIG. 10 shows a further testing apparatus which constitutes a modification of the apparatus of FIG. 9. All such parts of the apparatus of FIG. 10 which are identical with or clearly analogous to corresponding parts of the apparatus of FIG. 9 are designated by similar reference characters plus 100.

The testing device or unit 754 of FIG. 10 and the measuring or evaluating circuit 757 of the testing device 754 are identical with the device 654 and circuit 657 of FIG. 9. The testing device or unit 756 includes a modified evaluating circuit 794 wherein the transducer 782 transmits electrical signals to a modified counter including a signal storing circuit 796 having n stages. The stages of the signal storing circuit 796 are further connected with the output of a second counter 787 which receives signals from the output of the AND-gate 784 in the evaluating circuit 757. When the counter 787 receives a first signal from the gate 784, it enables the transducer 782 to transmit a signal to the first stage a of the circuit 796. The transmission of a second signal to the input of the counter 787 triggers the transmission of a signal from the transducer 782 to the second stage b of the signal storing circuit 796, and so forth. Each stage of the circuit 796 stores the signal for the duration of one cycle, i.e., for an interval which is required to transmit to the circuit 787 n signals via gate 784 and counter 787. The output of each stage of the circuit 787 is connected with the input of an averaging circuit 797. The output of the averaging circuit 797 is connected with the gauge 791 and with the threshold circuits 788, 789 for the lamps 792, 793. The outputs of the threshold circuits 788, 789 are further connected to the inputs of an OR-gate 798 whose output is connected with the second stage 769b of the shift register 769.

The difference between the testing apparatus of FIGS. 9 and 10 is that the apparatus of FIG. 10 furnishes a continuous signal denoting the average permeability of a predetermined number of successively tested convoluted uniting bands B. It will be recalled that the averaging circuit 683 of FIG. 9 furnishes periodic signals to threshold circuits 688, 689 and gauge 691. Thus, the apparatus of FIG. 10 allows for practically instantaneous detection of deviations of permeability of several successively tested uniting bands B from an acceptable permeability. Deviations from acceptable range of permeabilities are indicated by the lamp 792 or 793, and the threshold circuit 788 or 789 also transmits a signal to the second stage 769b of the shift register 769 via OR-gate 798. This enables the shift register 769 to transmit such signals to the segregating unit 771 which causes the nozzle 776 to eject the cigarettes having defective uniting bands B. Furthermore, and as mentioned in connection with FIG. 9, the signals which are transmitted by the outputs of the threshold circuits 788, 789 can be used to effect automatic adjustments of the perforating unit 615 in the machine of FIG. 1. This insures that the unit 615 is adjusted practically simultaneously with detection of bands B whose permeability is not within the acceptable range.

The averaging operation of the evaluating circuit 794 is even more accurate (namely, more up to date) than that of the operation of the circuit 658. This is due to the fact that the signal at the output of the averaging circuit 797 invariably (i.e., at all times) denotes the average permeability of a predetermined number of uniting bands B whereby such predetermined number includes all uniting bands which have advanced beyond the second testing station in the testing device 756. Thus, the signal (from transducer 782) which denotes the foremost tested band B (forming part of a satisfactory wrapper) is eliminated from the averaging operation as soon as the transducer 782 transmits a fresh signal. Therefore, the signals which are transmitted by the threshold circuits 788 and 789 can be used for adjustment of the perforating unit as well as for segregation of respective cigarettes Z because they insure that the unit 771 expels only those cigarettes whose uniting bands B are unsatisfactory.

The apparatus of FIG. 9 or 10 can be simplified if the manufacturer desires to ascertain whether or not the permeability of uniting bands B is below a minimum acceptable value, i.e., if the manufacturer wishes to rely solely on the evaluating circuit 657 or 757 for detection of those wrappers whose permeability is excessive (due to excessive permeability of the wrapper of the plain cigarette T and/or due to excessive permeability of the uniting band B). In such simplified apparatus, the threshold circuit 689 or 789 and the lamp 693 or 793 can be dispensed with.

The testing devices 654, 754 are preferably installed ahead of the testing devices 656, 756 (or vice versa) in order to insure that signals which are transmitted to the measuring circuits 657, 757 do not interfere with signals which are transmitted to the measuring circuits 658, 794 (or vice versa). The shift registers 669, 769 constitute relatively simple time-delay means which insure that the respective averaging circuit receives timely signals from the measuring circuit 657 or 757.

An important advantage of the improved method and apparatus is that they insure reliable detection of cigarettes wherein the wrappers (when considered as a whole or when one considers only the wrappers of plain cigarettes) are clearly defective so that the cigarettes cannot be admitted into the packing machine, as well as that they insure reliable detection of cigarettes wherein the permeability of predetermined portions (bands B) of the wrappers is unsatisfactory. Moreover, such monitoring of entire wrappers, of major portions of wrappers (i.e., of the wrappers of plain cigarettes) and/or of predetermined (relatively small) portions of the wrappers can be effected by resorting to relatively simple instrumentalities many components of which can correspond to those of presently known testing apparatus which have been found to be highly satisfactory for use in machines for the production of rod-shaped articles constituting or forming part of smokers' products. Still further, the improved method and apparatus render it possible to monitor the overall permeability of wrappers with a first degree of accuracy, to monitor the permeability of predetermined portions of wrappers with a second degree of accuracy and/or to change the acceptable range of permeabilities for the entire wrappers or for predetermined portions of wrappers practically at will. This renders it possible to take into account all factors which influence the permeability of wrappers, such as the density of fillers of cigarettes or the like, the initial (inherent) permeability of the material of the wrappers, the setting of the perforating device or devices and/or others.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the claims.

What is claimed is:

1. A method of testing wrappers of rod-shaped articles which constitute or form part of smokers' products, comprising the steps of measuring the permeability of at least the major portion of the wrapper of each of a series of successive articles; comparing the measured permeability with a predetermined value denoting the maximum permissible permeability of such portions of wrappers; measuring the permeability of predetermined portions of the wrappers of said series of articles, each of said measuring steps including establishing a pressure differential between the interior and the exterior of the respective wrappers; moving the articles of said series sideways along a predetermined path in the course of said measuring steps; generating signals denoting the permeability of said predetermined wrapper portions; and comparing said signals with a signal denoting the minimum acceptable permeability of said predetermined wrapper portions.

2. A method of testing the wrappers of rod-shaped articles which constitute or form part of smokers' products, comprising the steps of measuring the permeability of at least the major portion of the wrapper of each of a series of successive articles; comparing the measured permeability with a predetermined value denoting the maxiumum permissible permeability of such portions of wrappers; measuring the permeability of predetermined portions of the wrappers of said series of articles, each of said measuring steps including establishing a pressure differential between the interior and the exterior of the respective wrappers; moving the articles of said series sideways along a predetermined path in the course of said measuring steps, said first and said last mentioned measuring steps being carried out in one and the same portion of said path; and generating signals denoting the permeability of said predetermined wrapper portions.

3. A method of testing the wrappers of rod-shaped articles which constitute or form part of smokers' products, comprising the steps of measuring the permeability of at least the major portion of the wrapper of each of a series of successive articles; comparing the measured permeability with a predetermined value denoting the maximum permissible permeability of such portions of wrappers; measuring the permeability of predetermined portions of the wrappers of said series of articles; generating signals denoting the permeability of said predetermined wrapper portions; comparing said signals with a signal denoting the minimum acceptable permeability of said predetermined wrapper portions; and segregating from said series those articles wherein the permeability of said predetermined wrapper portions is less than said minimum acceptable permeability.

4. A method as defined in claim 3, further comprising the step of moving the articles of said series sideways along a predetermined path in the course of said measuring steps, each of said measuring steps including establishing a pressure differential between the interior and the exterior of the respective wrappers.

5. A method as defined in claim 4, further comprising the step of making holes in said predetermined wrapper portions prior to said last mentioned measuring step.

6. A method as defined in claim 4, wherein the pressure differntial which is established in the course of said first mentioned measuring step deviates from the pressure differential which is established in the course of said last mentioned measuring step.

7. A method as defined in claim 4, wherein said signal generating step includes generating signals denoting the average permeability of a plurality of successively tested predetermined wrapper portions.

8. A method as defined in claim 4, wherein said signal generating step includes generating a discrete signal for the predetermined wrapper portion of each of said series of articles.

9. A method as defined in claim 4, wherein said first and last mentioned measuring steps are carried out in discrete first and second portions of said path.

10. A method as defined in claim 4, wherein said major portion of each wrapper includes said predetermined portion of the respective wrapper.

11. A method as defined in claim 4, wherein the permeability of said predetermined portion of each wrapper is measured solely in the course of said last mentioned measuring step.

12. A method as defined in claim 4, wherein said predetermined portion of each wrapper constitutes a relatively small part of the respective wrapper.

13. A method as defined in claim 3, further comprising the step of segregating from said series those articles whose wrappers exhibit a permeability exceeding said predetermined value.

14. A method as defined in claim 3, further comprising the step of converting a plurality of successive signals denoting the permeability of predetermined portions of wrappers whose permeability is less than said predetermined permeability into a second signal denoting the average permeability of the respective number of predetermined wrapper portions.

15. A method as defined in claim 14, wherein said number is constant.

16. A method as defined in claim 15, wherein said converting step includes modifying said second signals upon completion of each second measuring step so that said second signal continuously denotes the average permeability of said constant number of predetermined portions including the last-tested predetermined portion.

17. A method as defined in claim 14, further comprising the step of comparing said second signal with a signal denoting the maximum permissible average permeability of a number of predetermined wrapper portions.

18. A method as defined in claim 17, further comprising the step of segregating from other articles at least some articles which include predetermined wrapper portions forming part of a number of predetermined wrapper portions whose average permeability exceeds said maximum permissible average permeability.

19. A method of testing the wrappers of rod-shaped articles which constitute or form part of smokers' products, comprising the steps of measuring the permeability of at least the major portion of the wrapper of each of a series of successive articles; comparing the measured permeability with a predetermined value denoting the maximum permissible permeability of such portions of wrappers; measuring the permeability of predetermined portions of the wrappers of said series of articles; generating signals denoting the permeability of said predetermined wrapper portions; converting a plurality of successive signals denoting the permeability of predetermined portions of wrappers whose permeability is less than said predetermined permeability into a second signal denoting the average permeability of the respective number of predetermined wrapper portions; and comparing said second signal with a signal denoting the minimum acceptable average permeability of said number of predetermined wrapper portions.

20. A method as defined in claim 19, further comprising the step of segregating from other articles at least some articles which include predetermined wrapper portions forming part of a number of predetermined wrapper portions whose average permeability is less than said minimum acceptable average permeability.

21. A method of testing the wrappers of rod-shaped articles which constitute or form part of smokers' products, comprising the steps of measuring the permeability of at least the major portion of the wrapper of each of a series of successive articles; comparing the measured permeability with a predetermined value denoting the maximum permissible permeability of such portions of wrappers; measuring the permeability of predetermined portions of the wrappers of said series of articles; generating signals denoting the permeability of said predetermined wrapper portions; converting a plurality of successive signals denoting the permeability of predetermined portions of wrappers whose permeability is less than said predetermined permeability into a second signal denoting the average permeability of the respective number of predetermined wrapper portions; and comparing said second signal with first and second reference signals respectively denoting the minimum acceptable and maximum permissible permeability of said number of predetermined wrapper portions.

22. A method as defined in claim 21, further comprising the step of segregating from other articles at least some articles which include predetermined wrapper portions forming part of a number of predetermined wrapper portions whose average permeability is less than said minimum acceptable or exceeds said maximum permissible average permeability.

23. Apparatus for testing the wrappers of rod-shaped articles which constitute or form part of smokers' products and wherein a predetermined portion of the wrapper of each article has holes for admission of atmospheric air, comprising means for moving a series of successive articles along a predetermined path, said moving means comprising an endless conveyor having a plurality of article receiving means arranged to move the articles sideways; a first testing device including means for measuring the permeability of at least the major portion of the wrapper of each article in said path and means for comparing the measured permeability with a predetermined value denoting the maximum permissible permeability of said major portions of wrappers; and a second testing device including means for measuring the permeability of said predetermined portions of the wrappers of said series of articles in said path, each of said measuring means including means for establishing a pressure differential between the interior and exterior of the wrappers, the magnitude of said pressure differential being indicative of permeability of the respective wrapper portions, the measuring means of said first testing device further including means for generating first signals denoting the permeability of said major portions of the respective wrappers and said comparing means including means for comparing said first signals with a reference signal denoting said predetermined value and for generating third signals denoting deviations of said first signals from said reference signal, said pressure differential establishing means of the measuring means of said second testing device having a portion of maximum sensitivity in the region of holes of said predetermined wrapper portions.

24. Apparatus as defined in claim 23, further comprising means for segregating from said series those articles wherein the permeability of said major wrapper portions exceeds said maximum permissible permeability.

25. Apparatus for testing the wrappers of rod-shaped articles which constitute or form part of smokers' products, comprising means for moving a series of successive articles along a predetermined path; a first testing device including means for measuring the permeability of at least the major portion of the wrapper of each article in said path and means for comparing the measured permeability with a predetermined value denoting the maximum permissible permeability of said portions of wrappers; and a second testing device including means for measuring the permeability of predetermined portions of the wrappers of said series of articles in said path, said last mentioned measuring means including means for generating discrete signals denoting the permeability of successively tested predetermined wrapper portions, said second testing device further comprising means for comparing said discrete signals with a reference signal denoting the minimum acceptable permeability of said predetermined wrapper portions and for generating third signals denoting deviations of said discrete signals from said reference signal.

26. Apparatus for testing the wrappers of rod-shaped articles which constitute or form part of smokers' products, comprising means for moving a series of successive articles along a predetermined path; a first testing device including means for measuring the permeability of at least the major portion of the wrapper of each article in said path and means for comparing the measured permeability with a predetermined value denoting the maximum permissible permeability of said portions of wrappers; a second testing device including means for measuring the permeability of predetermined portions of the wrappers of said series of articles in said path, means for comparing the measured permeability of said predetermined wrapper portions with a second predetermined value denoting the minimum acceptable permeability of said predetermined wrapper portions; and means for segregating from said series those articles wherein the permeability of said predetermined wrapper portion is less than said minimum acceptable permeability.

27. Apparatus as defined in claim 25, wherein said moving means comprises an endless conveyor having a plurality of article receiving means arranged to move the articles sideways, each of said measuring means including means for establishing a pressure differential between the interior and exterior of the wrappers, the magnitude of said pressure differential being indicative of permeability of the respective wrapper portions.

28. Apparatus as defined in claim 26, wherein the measuring means of said second testing device includes means for generating signals denoting the average permeability of a plurality of successively tested predetermined wrapper portions.

29. Apparatus as defined in claim 26, wherein the measuring means of said second testing device includes means for generating discrete signals denoting the permeability of successively tested predetermined wrapper portions.

30. Apparatus as defined in claim 26, wherein said first and second testing devices are adjacent to discrete first and second portions of said path.

31. Apparatus as defined in claim 26, wherein the measuring means of said first testing device includes means for establishing a pressure differential between the interior and exterior of said major portions of wrappers of successive articles, said major portion of each wrapper including the respective predetermined portion.

32. Apparatus as defined in claim 26, wherein said predetermined wrapper portions are outside of the range of the measuring means of said first testing device.

33. Apparatus as defined in claim 26, wherein the measuring means of said second testing device includes means for establishing a pressure differential solely between the interior and exterior of said predetermined wrapper portions.

34. Apparatus as defined in claim 26, wherein at least the measuring means of said first testing device includes means for establishing a pressure differential between the interior and exterior of successive wrappers, the magnitude of said pressure differential being indicative of permeability of the respective wrapper portions, said last mentioned measuring means further including electropneumatic transducer means operative to transmit to said comparing means first signals denoting the respective pressure differentials, said comparing means including means for comparing said first signals with a reference signal denoting said predetermined value and for producing third signals denoting deviations of said first signals from said reference signal.

35. Apparatus for testing the wrappers of rod-shaped articles which constitute or form part of smokers' products, comprising means for moving a series of successive articles along a predetermined path; a first testing device including means for measuring the permeability of at least the major portion of the wrapper of each article in said path and means for comparing the measured permeability with a predetermined value denoting the maximum permissible permeability of said portions of wrappers; and a second testing device including means for measuring the permeability of predetermined portions of the wrappers of said series of articles in said path, said last mentioned measuring means including means for generating first signals denoting the permeability of said predetermined portions of the wrappers of said series of articles in said path and means for converting a number of successive first signals denoting the permeability of predetermined portions of wrappers whose permeability is less than said predetermined value into second signals denoting the average permeability of the respective predetermined wrapper portions.

36. Apparatus as defined in claim 35, wherein said measuring means of said first testing device includes means for preventing the transmission to said converting means of those first signals which denote the permeability of predetermined wrapper portions forming part of wrappers whose permeability exceeds said predetermined value.

37. Apparatus as defined in claim 36, wherein the measuring means of said second testing device further comprises counter means for the predetermined portions of those wrappers whose permeability is less than said predetermined value.

38. Apparatus as defined in claim 35, wherein said measuring means of said second testing device further comprises means for comparing said second signals with a signal denoting the minimum average permeability of said number of predetermined wrapper portions.

39. Apparatus as defined in claim 35, wherein said measuring means of said second testing device further comprises means for comparing said second signals with a signal denoting the maximum permissible average permeability of said number of predetermined wrapper portions.

40. Apparatus as defined in claim 38, wherein one of said testing devices is located ahead of the other of said testing devices, as considered in the direction of movement of articles along said path.

41. Apparatus as defined in claim 40, wherein said one testing device is said first testing device and said measuring means of said first testing device comprises means for generating third signals denoting those major wrapper portions whose permeability is below said predetermined value and time-delay means for transmitting said third signals to the measuring means of said second testing device.

42. Apparatus as defined in claim 35, wherein said measuring means of said first testing device includes means for generating third signals denoting the articles with major wrapper portions whose permeability exceeds said predetermined value, and further comprising means for expelling such articles from said path.

43. Apparatus as defined in claim 35, wherein said measuring means of said second testing device further comprises means for comparing said second signals with a reference signal denoting the minimum acceptable average permeability of said number of predetermined wrapper portions, and further comprising means for expelling from said path at least some articles having predetermined wrapper portions whose monitoring resulted in the generation of second signals denoting average permeability less than said minimum acceptable average permeability.

44. Apparatus as defined in claim 35, wherein said measuring means of said second testing device further comprises means for comparing said second signals with a reference signal denoting the maximum permissible average permeability of said number of predetermined wrapper portions, and further comprising means for expelling from said path at least some articles having predetermined wrapper portions whose monitoring resulted in the generation of second signals denoting average permeability exceeding said maximum permissible average permeability.

45. Apparatus for testing the wrappers of rod-shaped articles which constitute or form part of smokers' products, comprising means for moving a series of successive articles along a predetermined path; a first testing device including means for measuring the permeability of at least the major portion of the wrapper of each article in said path and means for comparing the measured permeability with a predetermined value denoting the maximum permissible permeability of said portions of wrappers; and a second testing device including means for measuring the permeability of predetermined portions of the wrappers of said series of articles in said path, said testing devices being adjacent to one and the same portion of said path.

* * * * *